(12) United States Patent
Arai et al.

(10) Patent No.: US 11,744,537 B2
(45) Date of Patent: Sep. 5, 2023

(54) RADIOGRAPHY SYSTEM, MEDICAL IMAGING SYSTEM, CONTROL METHOD, AND CONTROL PROGRAM

(71) Applicant: FUJIFILM Corporation, Tokyo (JP)

(72) Inventors: Takahisa Arai, Kanagawa (JP); Hiroki Nakayama, Kanagawa (JP); Yoshie Fujimoto, Kanagawa (JP); Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 73 days.

(21) Appl. No.: 16/880,910

(22) Filed: May 21, 2020

(65) Prior Publication Data
US 2020/0375562 A1 Dec. 3, 2020

(30) Foreign Application Priority Data
May 29, 2019 (JP) .................. 2019-100679

(51) Int. Cl.
*A61B 6/00* (2006.01)
*A61B 6/04* (2006.01)
(Continued)

(52) U.S. Cl.
CPC ............ *A61B 6/502* (2013.01); *A61B 6/0414* (2013.01); *A61B 6/461* (2013.01); *A61B 6/5247* (2013.01);
(Continued)

(58) Field of Classification Search
CPC ....... A61B 6/502; A61B 6/0414; A61B 6/461; A61B 6/5247; A61B 6/54; A61B 8/0825;
(Continued)

(56) References Cited

U.S. PATENT DOCUMENTS

2006/0029268 A1\* 2/2006 Endo .................. G06T 11/008
382/132
2006/0034503 A1 2/2006 Shimayama
(Continued)

FOREIGN PATENT DOCUMENTS

JP 2001-340327 A 12/2001
JP 2006-051198 A 2/2006
(Continued)

OTHER PUBLICATIONS

The extended European search report issued by the European Patent Office dated Oct. 28, 2020, which corresponds to European Patent Application No. 20177067.4-1122 and is related to U.S. Appl. No. 16/880,910.
(Continued)

*Primary Examiner* — Keith M Raymond
*Assistant Examiner* — Sean A Frith
(74) *Attorney, Agent, or Firm* — Studebaker & Brackett PC

(57) ABSTRACT

A compression plate of a mammography apparatus has an upper surface which is irradiated with radiation, a lower surface which is opposite to the upper surface and comes into contact with the breast, and a surface which is parallel to the upper surface between the upper surface and the lower surface. In the compression plate, a compression plate scale for identifying an in-plane position of each surface is given to any one of the surfaces. A first display control unit of a console performs control to display a radiographic image captured by the mammography apparatus on a display unit. A second display control unit of the console performs control to display an image scale which indicates a position on the radiographic image corresponding to the in-plane position of the compression plate on the radiographic image displayed on the display unit.

22 Claims, 24 Drawing Sheets

(51) Int. Cl.
*A61B 8/08* (2006.01)
*A61B 8/00* (2006.01)
*G01T 1/161* (2006.01)

(52) U.S. Cl.
CPC .............. *A61B 6/54* (2013.01); *A61B 8/0825* (2013.01); *A61B 8/403* (2013.01); *A61B 8/5261* (2013.01); *A61B 8/54* (2013.01); *G01T 1/161* (2013.01)

(58) Field of Classification Search
CPC ......... A61B 8/403; A61B 8/5261; A61B 8/54; G01T 1/161
See application file for complete search history.

(56) References Cited

U.S. PATENT DOCUMENTS

| | | | |
|---|---|---|---|
| 2008/0240346 A1* | 10/2008 | Kashiwagi | A61B 6/0414 378/37 |
| 2008/0273657 A1* | 11/2008 | Klausz | A61B 6/4441 378/21 |
| 2009/0118614 A1* | 5/2009 | Sendai | A61B 6/037 600/437 |
| 2009/0234229 A1* | 9/2009 | Mikami | A61B 6/4494 600/445 |
| 2010/0061521 A1* | 3/2010 | Standar | G09F 13/20 378/162 |
| 2010/0246924 A1 | 9/2010 | Morita | |
| 2011/0230759 A1 | 9/2011 | Muller | |
| 2014/0037068 A1* | 2/2014 | Burion | A61B 34/25 378/95 |
| 2014/0093036 A1* | 4/2014 | Masumoto | A61B 6/5205 378/41 |
| 2015/0187119 A1 | 7/2015 | Masumoto | |
| 2016/0110875 A1* | 4/2016 | Sugiyama | G06T 7/0012 382/131 |
| 2016/0120407 A1* | 5/2016 | Martinez-Lorenzo | A61B 6/502 600/427 |
| 2016/0310215 A1* | 10/2016 | Palma | A61B 34/10 |
| 2017/0128037 A1* | 5/2017 | Mori | A61B 6/502 |
| 2017/0281131 A1 | 10/2017 | Sendai | |
| 2018/0070892 A1* | 3/2018 | Sugiyama | A61B 6/502 |
| 2018/0168780 A1* | 6/2018 | Kopelman | G06K 9/6212 |
| 2018/0338795 A1* | 11/2018 | Sugiyama | A61B 10/0041 |
| 2019/0125301 A1* | 5/2019 | Jago | A61B 8/0825 |
| 2019/0200955 A1* | 7/2019 | Ryu | A61B 8/463 |
| 2019/0251327 A1* | 8/2019 | Laviola | A61B 8/5261 |

FOREIGN PATENT DOCUMENTS

| | | |
|---|---|---|
| JP | 2006-280444 A | 10/2006 |
| JP | 2009-219656 A | 10/2009 |
| JP | 2010-253245 A | 11/2010 |
| JP | 2011-200655 A | 10/2011 |
| JP | 2014-054398 A | 3/2014 |
| JP | 2014-155207 A | 8/2014 |
| JP | 2017-176509 A | 10/2017 |

OTHER PUBLICATIONS

"Notice of Reasons for Refusal" Office Action issued in JP 2019-100679; mailed by the Japanese Patent Office dated Jun. 21, 2022.

* cited by examiner

FIG. 5A

| TYPE OF COMPRESSION PLATE (COMPRESSION PLATE ID) | IMAGE SCALE (IMAGE SCALE ID) |
|---|---|
| B0010 | NONE |
| B0021 | S0021 |
| B0022 | S0022 |
| B0023 | S0023 |
| B0031 | S0031 |
| B0032 | S0032 |
| B0033 | S0033 |
| B0041 | S0041 |
| …… | …… |

FIG. 5B

| TYPE OF COMPRESSION PLATE (COMPRESSION PLATE ID) | TYPE OF IMAGING | IMAGE SCALE (IMAGE SCALE ID) |
|---|---|---|
| B0010 | ----- | NONE |
| B0020 | CC | S0021 |
| B0020 | MLO (RIGHT) | S0022 |
| B0020 | MLO (LEFT) | S0023 |
| B0030 | CC | S0031 |
| B0030 | MLO (RIGHT) | S0032 |
| B0030 | MLO (LEFT) | S0033 |
| …… | …… | …… |

| TYPE OF COMPRESSION PLATE (COMPRESSION PLATE ID) | IRRADIATION FIELD | IMAGE SCALE (IMAGE SCALE ID) |
|---|---|---|
| B0010 | ----- | NONE |
| B0021 | ****1 | S0121 |
|  | %%%%1 | S0221 |
|  | &&&&1 | S0321 |
| B0022 | ****1 | S0122 |
|  | %%%%1 | S0222 |
|  | &&&&1 | S0322 |
| ...... | ...... | ...... |

US 11,744,537 B2

RADIOGRAPHY SYSTEM, MEDICAL IMAGING SYSTEM, CONTROL METHOD, AND CONTROL PROGRAM

CROSS-REFERENCE TO RELATED APPLICATION

The present application claims priority under 35 U.S.C. § 119 to Japanese Patent Application No. 2019-100679, filed on May 29, 2019, which is hereby expressly incorporated by reference, in its entirety, into the present application.

BACKGROUND

Technical Field

The present disclosure relates to a radiography system, a medical imaging system, a control method, and a control program.

Related Art

A radiography apparatus has been known which compresses and fixes the breast of a subject with a compression member, irradiates the breast in the compressed state with radiation emitted from a radiation source, and detects the radiation transmitted through the breast with a radiation detector to capture a radiographic image.

For example, Japanese Patent Application Laid-Open (JP-A) No. 2006-280444 discloses a technique which captures a radiographic image of the breast compressed by a compression member, specifies the position of a lesion from the captured radiographic image, and treats the specified position of the lesion in the breast that remains compressed. In the technique disclosed in JP-A 2006-280444, a marker is provided on the compression member and the marker provided on the compression member is included in the radiographic image. Therefore, the position of the lesion to be treated is specified by the position of the image of the marker in the radiographic image.

An ultrasonography apparatus has been known which scans the breast of the subject with an ultrasound probe to capture an ultrasound image of the breast. An apparatus is disclosed which can continuously capture a radiographic image and an ultrasound image while maintaining the compression of the breast by a compression member.

In a case in which an ultrasound image is captured with reference to the radiographic image of the breast in the compressed state, for example, the breast in the radiographic image and the breast in the compressed state may be different in appearance. Therefore, in some cases, it is difficult to understand the correspondence between a position on the radiographic image and a position on the compression member. As such, in a case in which a radiographic image and an ultrasound image are continuously captured, the application of the technique disclosed in Patent Document 1 may not be enough to check a position on the compression member which corresponds to a position on the radiographic image.

SUMMARY

The present disclosure has been made in view of the above-mentioned problems and an object of the present disclosure is to provide a radiography system, a medical imaging system, a control method, and a control program that enable a user to easily understand a correspondence between a position on a radiographic image and a position on a compression member.

In order to achieve the above object, according to a first aspect of the present disclosure, there is provided a radiography system comprising: a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures a radiographic image of the breast in the compressed state using the radiation detector; a first display control unit that performs control to display the radiographic image captured by the mammography apparatus on a display device; and a second display control unit that performs control to display second position identification information which indicates a position on the radiographic image corresponding to the in-plane position of the compression member and corresponds to the first position identification information on the radiographic image displayed on the display device.

In order to achieve the above object, according to a second aspect of the present disclosure, there is provided a radiography system comprising: a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures a radiographic image of the breast in the compressed state using the radiation detector; a first display control unit that performs control to display the radiographic image captured by the mammography apparatus on a display device; and a second display control unit that performs control to display second position identification information which indicates a position on the radiographic image corresponding to the in-plane position of the compression member and corresponds to the first position identification information on the radiographic image displayed on the display device.

According to a third aspect of the present disclosure, in the radiography system according to the first aspect or the second aspect, the second display control unit may perform control to display the second position identification information in a case in which the compression member maintains the compressed state for a predetermined time or more after the radiographic image is captured.

According to a fourth aspect of the present disclosure, in the radiography system according to the first aspect or the second aspect, the second display control unit may perform control to display the second position identification information in a case in which continuous imaging that captures an ultrasound image of the breast while maintaining the compressed state after capturing the radiographic image.

According to a fifth aspect of the present disclosure, the radiography system according to the fourth aspect may further comprise an acquisition unit that acquires mammary gland amount information indicating an amount of mammary gland in the breast. The second display control unit may perform the continuous imaging in a case in which the amount of mammary gland indicated by the mammary gland amount information is equal to or greater than a predetermined amount of mammary gland.

According to a sixth aspect of the present disclosure, the radiography system according to the fourth aspect may further comprise an acquisition unit that acquires region information indicating a mammary gland region in the breast on the basis of the radiographic image. The second display control unit may perform the continuous imaging in a case in which a size of the mammary gland region indicated by the region information is equal to or greater than a predetermined size.

According to a seventh aspect of the present disclosure, in the radiography system according to any one of the fourth to sixth aspects, in a case in which the continuous imaging is performed and the radiographic image includes a plurality of mammary gland regions, the second display control unit may display the second position identification information in different forms in a mammary gland region for which the capture of the ultrasound image has ended and a mammary gland region for which the capture of the ultrasound image has not ended.

According to an eighth aspect of the present disclosure, in the radiography system according to any one of the fourth to sixth aspects, the second display control unit may end the display of the second position identification information in a case in which the capture of the ultrasound image has ended.

According to a ninth aspect of the present disclosure, in the radiography system according to any one of the first to seventh aspects, the second display control unit may end the display of the second position identification information in a case in which the compression of the breast by the compression member is released after the second position identification information is displayed.

According to a tenth aspect of the present disclosure, in the radiography system according to any one of the first to ninth aspects, the radiographic image may not include an image of the first position identification information.

According to an eleventh aspect of the present disclosure, the radiography system according to any one of the first to tenth aspects may further comprise a detection unit that detects a type of the compression member. The first position identification information may be predetermined according to the type of the compression member and the second display control unit may perform control to display the second position identification information corresponding to the type of the compression member detected by the detection unit.

According to a twelfth aspect of the present disclosure, in the radiography system according to any one of the first to eleventh aspects, in a case in which the mammography apparatus includes a compression member to which the first position identification information is not given, instead of the compression member to which the first position identification information is given, and captures the radiographic image of the breast compressed by the compression member to which the first position identification information is not given, the second display control unit may perform control not to display the second position identification information.

According to a thirteenth aspect of the present disclosure, in the radiography system according to any one of the first to twelfth aspects, the second display control unit may perform control to display the second position identification information in the mammary gland region of the breast included in the radiographic image.

According to a fourteenth aspect of the present disclosure, the radiography system according to any one of the first to thirteenth aspects may further comprise a receiving unit that receives designation of a position on the radiographic image displayed on the display device. The second display control unit may perform control to display the second position identification information in a case in which the receiving unit receives the designation of the position on the radiographic image.

According to a fifteenth aspect of the present disclosure, the radiography system according to any one of the first to thirteenth aspects may further comprise a receiving unit that receives designation of a position on the radiographic image displayed on the display device. The second display control unit may perform control to display the second position identification information in a case in which the position on the radiographic image received by the receiving unit is a position in the mammary gland region of the breast.

According to a sixteenth aspect of the present disclosure, in the radiography system according to any one of the first to twelfth aspects, the second display control unit may perform control to display the second position identification information for the mammary gland region of the breast in the radiographic image and the second position identification information for a region other than the mammary gland region in different forms.

According to a seventeenth aspect of the present disclosure, in the radiography system according to the sixteenth aspect, in a case in which the radiographic image includes a plurality of the mammary gland regions, the second display control unit may display the second position identification information items for the mammary gland regions in different forms.

According to an eighteenth aspect of the present disclosure, in the radiography system according to any one of the first to seventeenth aspects, in a case in which the first display control unit changes a size of the radiographic image displayed on the display device, the second display control unit may perform control to change the display of the second position identification information, following the change in the size of the radiographic image.

According to a nineteenth aspect of the present disclosure, in the radiography system according to any one of the first to eighteenth aspects, the second display control unit may perform control to audibly display the second position identification information.

According to a twentieth aspect of the present disclosure, in the radiography system according to any one of the first to nineteenth aspects, the compression member may include: a first compression member that compresses the breast; and a second compression member which is attachable to and detachable from the first compression member and to which the first position identification information is give.

In order to achieve the above object, according to a twenty-first aspect of the present disclosure, there is provided a medical imaging system comprising: the radiography system according to any one of the first to twentieth aspects; and an ultrasonography apparatus that captures an ultrasound image of the breast compressed by the compression member.

In order to achieve the above object, according to a twenty-second aspect of the present disclosure, there is provided a control method comprising: performing control to display, on a display device, a radiographic image captured by a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device.

In order to achieve the above object, according to a twenty-third aspect of the present disclosure, there is provided a control method comprising: performing control to display, on a display device, a radiographic image captured by a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device.

In order to achieve the above object, according to a twenty-fourth aspect of the present disclosure, there is provided a control program that causes a computer to execute: performing control to display, on a display device, a radiographic image captured by a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device.

In order to achieve the above object, according to a twenty-fifth aspect of the present disclosure, there is provided a control program that causes a computer to execute: performing control to display, on a display device, a radiographic image captured by a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device.

Further, the radiography system according to the present disclosure is a radiography system having a processor. The processor performs control to display, on a display device, a radiographic image captured by a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures the radiographic image of the breast in the compressed state using the radiation detector, and performs control to display second position identification information which indicates a position on the radiographic image corresponding to the in-plane position of the compression member and corresponds to the first position identification information on the radiographic image displayed on the display device.

Furthermore, the radiography system according to the present disclosure is a radiography system having a processor. The processor performs control to display, on a display device, a radiographic image captured by a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures the radiographic image of the breast in the compressed state using the radiation detector, and performs control to display second position identification information which indicates a position on the radiographic image corresponding to the in-plane position of the compression member and corresponds to the first position identification information on the radiographic image displayed on the display device.

According to the present disclosure, the correspondence between a position on the radiographic image and a position on the compression member can be easily understood.

BRIEF DESCRIPTION OF THE DRAWINGS

FIG. 5A is a diagram illustrating an example of image scale information according to the first embodiment.

FIG. 5B is a diagram illustrating another example of the image scale information according to the first embodiment.

DESCRIPTION OF EMBODIMENTS

Hereinafter, embodiments of the invention will be described in detail with reference to the drawings. Each of the embodiments does not limit the invention.

First Embodiment

Figure 1:
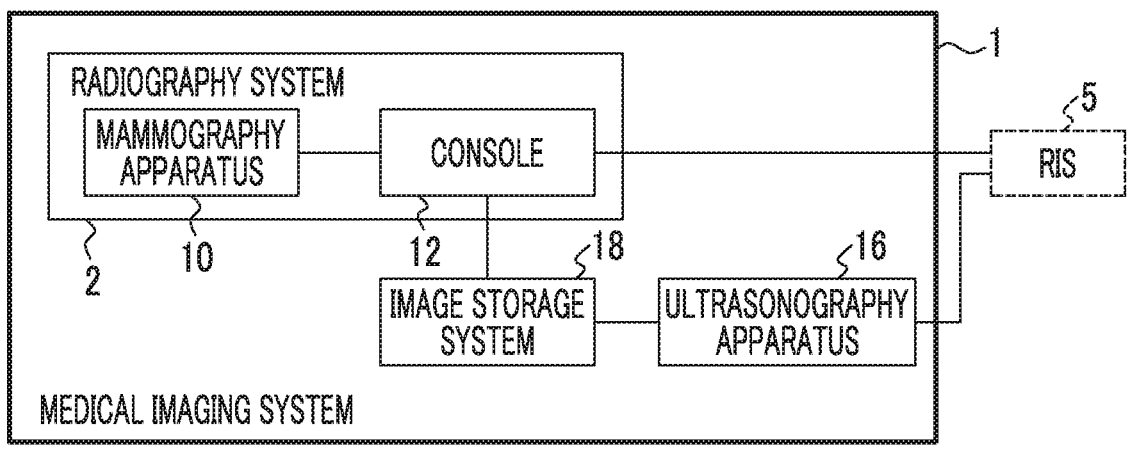
FIG. 1 is a diagram schematically illustrating an example of the overall configuration of a medical imaging system according to a first embodiment.

First, an example of the overall configuration of a medical imaging system according to this embodiment will be described. FIG. 1 is a diagram illustrating an example of the overall configuration of a medical imaging system 1 according to this embodiment.

As illustrated in FIG. 1, the medical imaging system 1 according to this embodiment comprises a radiography system 2, an ultrasonography apparatus 16, and an image storage system 18.

Figure 2:
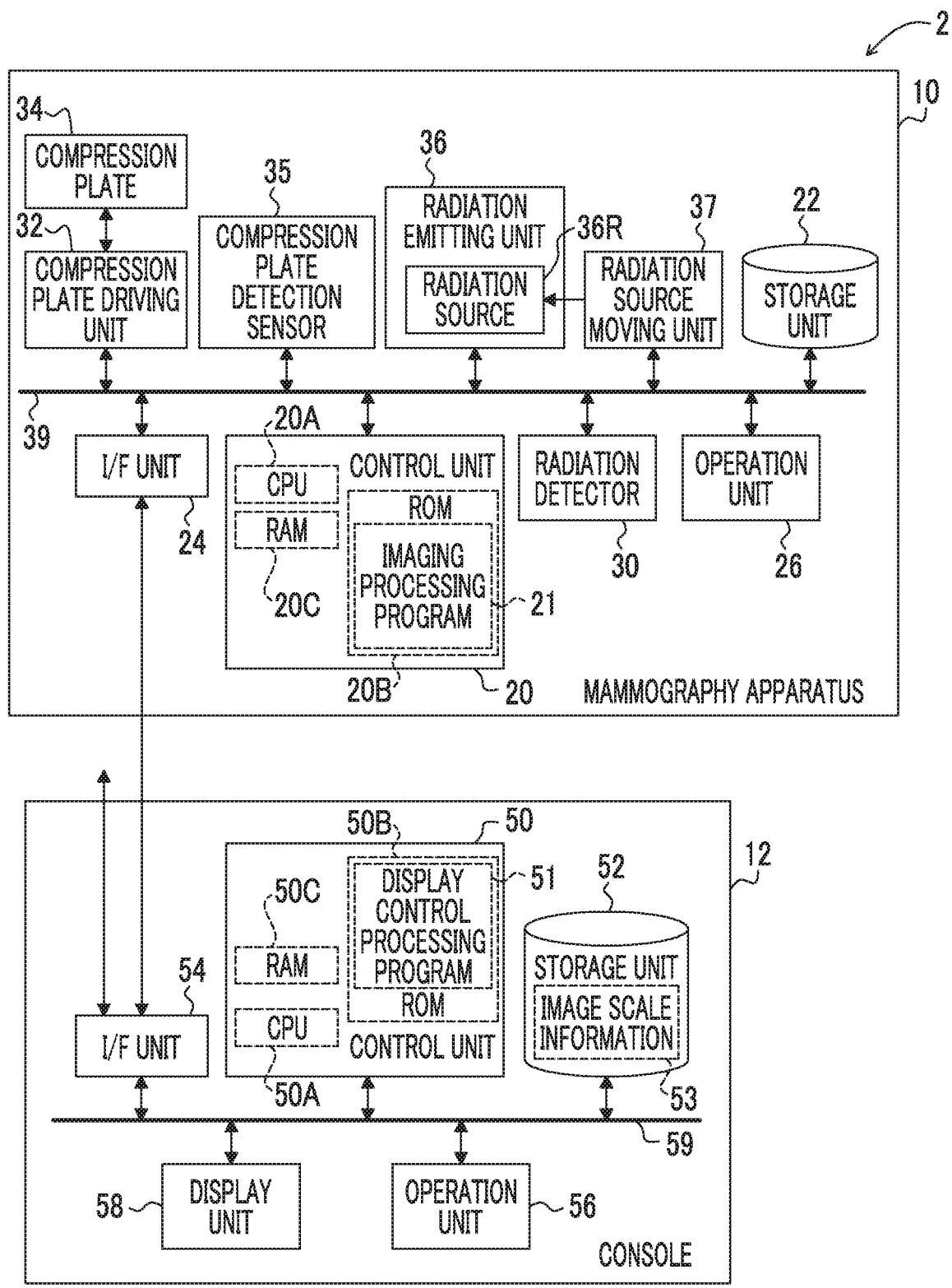
FIG. 2 is a block diagram illustrating an example of the configuration of a console and a mammography apparatus according to the first embodiment.
Figure 3:
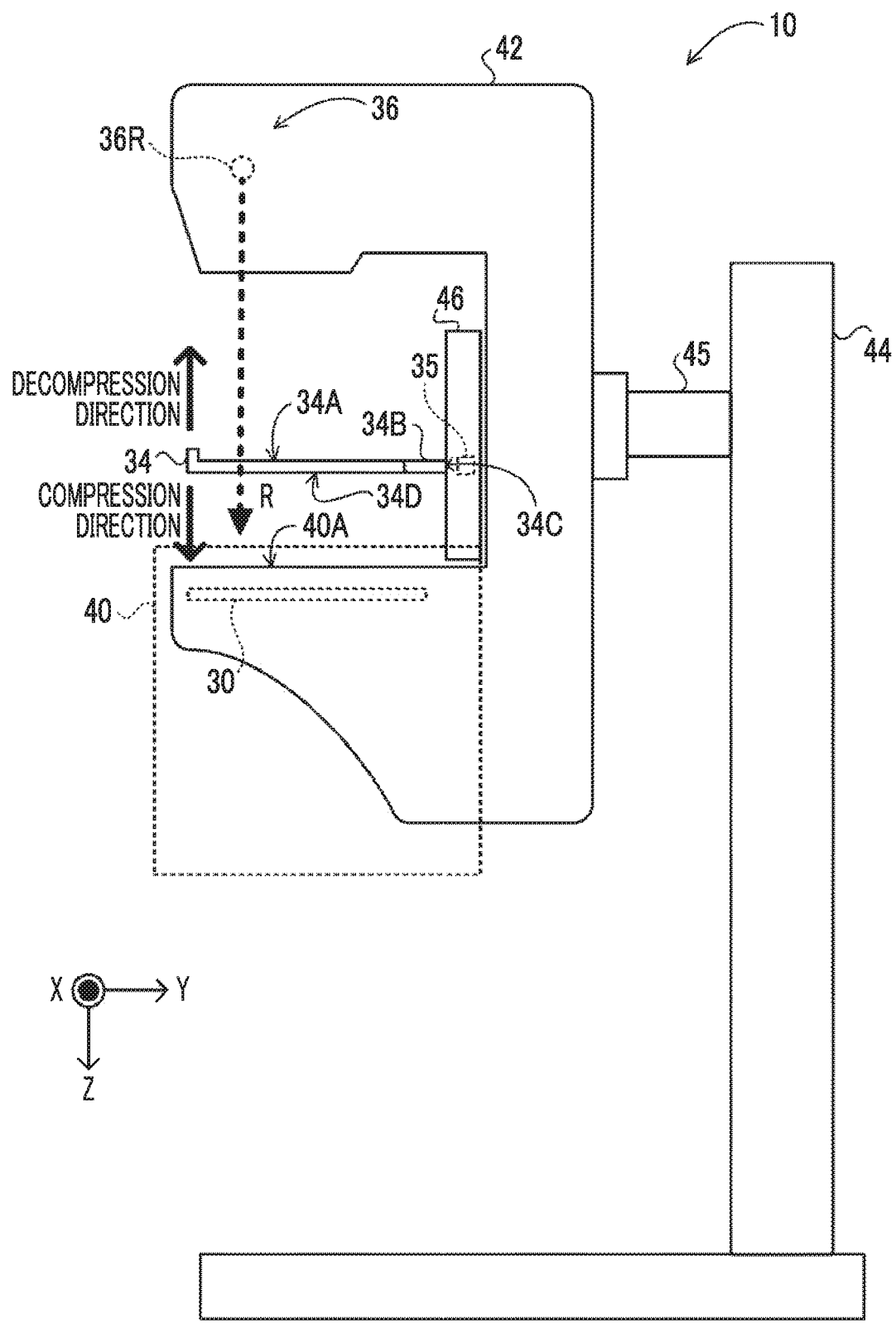
FIG. 3 is a side view illustrating an example of the outward appearance of the mammography apparatus according to the first embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the outward appearance of the mammography apparatus 10 according to this embodiment. FIG. 3 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, an interface (I/F) unit 24, an operation unit 26, a radiation detector 30, a compression plate driving unit 32, a compression plate 34, a compression plate detection sensor 35, a radiation emitting unit 36, and a radiation source moving unit 37. The control unit 20, the storage unit 22, the I/F unit 24, the operation unit 26, the radiation detector 30, the compression plate driving unit 32, the compression plate detection sensor 35, the radiation emitting unit 36, and the radiation source moving unit 37 are connected to each other through a bus 39, such as a system bus or a control bus, such that they can transmit and receive various kinds of information.

The control unit 20 according to this embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 according to this embodiment, in a case in which imaging is performed, the breast of the subject is positioned on an imaging surface 40A of the imaging table 40 by a user such as a doctor or a radiology technician. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data of the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 30 in the mammography apparatus 10 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a compression unit 46. In addition, as illustrated in FIG. 3, the mammography apparatus 10 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The radiation source moving unit 37 can relatively rotate the arm portion 42 with respect to the base 44, using the shaft portion 45 as a rotation axis.

In the mammography apparatus 10 according to this embodiment, at least two types of imaging can be performed to capture radiographic images. Specifically, the mammography apparatus 10 performs at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 36R in a case in which the radiation R is emitted from the radiation source 36R to the imaging table 40 in the capture of a radiographic image is referred to as an "imaging position".

In a case in which the CC imaging is performed, the imaging table 40 is adjusted to a state in which the imaging surface 40A faces the upper side of the mammography apparatus 10 (the head of the subject). In this case, the position of the radiation source 36R is adjusted to an imaging position that faces the imaging surface 40A of the imaging table 40. Therefore, the radiation R is emitted from the radiation source 36R to the breast in a direction from the head to the foot of the subject and the CC imaging is performed.

In contrast, in a case in which the MLO imaging is performed, the position of the imaging table 40 is adjusted to a state in which the imaging surface 40A is rotated up to a predetermined angle in a range of, for example, 45 degrees or more and less than 90 degrees with respect to the case in which the CC imaging is performed. Specifically, in a case in which an image of the left breast is captured, the imaging surface 40A is inclined to the right. In a case in which an image of the right breast is captured, the imaging surface 40A is inclined to the left. Therefore, the radiation R is emitted from the radiation source 36R to the breast in a direction from the center of the body of the subject to the outside (in a direction from a space between the breasts of the subject to the arm) and the MLO imaging is performed.

The compression plate driving unit 32 is provided in the compression unit 46 and a support portion 34B of the compression plate 34 is attached to the compression plate driving unit 32. A compression plate identifier (not illustrated) for identifying the type of the compression plate 34 (which will be described in detail below) is provided on a surface 34C of the compression plate 34 which is attached to the compression plate driving unit 32. The compression unit 46 is provided with the compression plate detection sensor 35. In a case in which the support portion 34B of the compression plate 34 is attached to the compression plate driving unit 32, the compression plate detection sensor 35 reads the compression plate identifier provided on the surface 34C and detects the type of the attached compression plate 34. The compression plate 34 according to this embodiment is an example of a compression member according to the present disclosure.

Each of the compression unit 46 and the arm portion 42 can be relatively rotated with respect to the base 44, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member and is moved in the up-down direction (Z-axis direction) by the compression plate driving unit 32 to compress the breast of the subject against the imaging table 40. As illustrated in FIG. 3, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction".

It is preferable that the compression plate 34 is optically transparent in order to check positioning or a compressed state in the compression of the breast. In addition, the compression plate 34 is made of a material having high transmittance for the radiation R. It is desirable that the compression plate 34 is made of a material that facilitates the transmission of ultrasonic waves from an ultrasound probe 65 (see FIG. 7, which will be described in detail below) of the ultrasonography apparatus 16. Examples of the material forming the compression plate 34 include resins such as polymethylpentene, polycarbonate, acrylic, and polyethylene terephthalate. In particular, polymethylpentene is suitable as the material forming the compression plate 34 since it has low rigidity, high elasticity, and high flexibility and has suitable values for acoustic impedance that affects the reflectance of ultrasonic waves and an attenuation coefficient that affects the attenuation of ultrasonic waves. The member forming the compression plate 34 is not limited to this embodiment. For example, the member forming the compression plate 34 may be a film-like member.

Figure 4A:
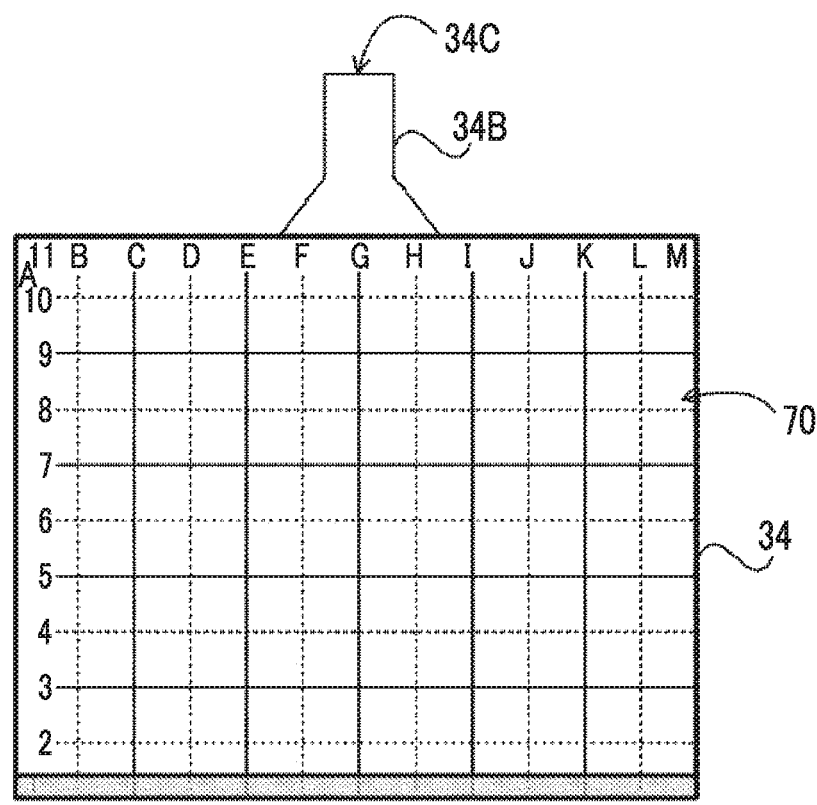
FIG. 4A is a plan view illustrating an example of a state in which a compression plate according to the first embodiment is viewed from the upper side.

Further, as illustrated in FIG. 4A, a compression plate scale 70 for identifying an in-plane position of the upper surface 34A which corresponds to a position on the radiographic image captured by the radiation detector 30 is provided on the upper surface 34A of the compression plate 34 according to this embodiment. In other words, the compression plate scale 70 for identifying a position on the compression plate 34 is provided on the upper surface 34A of the compression plate 34. The upper surface 34A according to this embodiment is an example of a first surface according to the present disclosure and the compression plate scale 70 according to this embodiment is an example of first position identification information according to the present disclosure. As described above, the first surface according to the present disclosure is a surface (the upper surface 34A in this embodiment) of the compression plate 34 which is irradiated with radiation, that is, a surface of the compression plate 34 which is closer to the radiation source 36R.

For example, the radiographic image displayed on the display unit 58 of the console 12 and the breast compressed by the compression plate 34 are different from each other in appearance. For example, in some cases, the size of the image of the breast in the displayed radiographic image is different from the size of the actual breast in the compressed state. Therefore, in some cases, it is difficult to understand the correspondence between a position on the radiographic image and a position on the compression plate 34. For example, in a case in which an ultrasound image is captured, an ultrasound image of the entire breast may not be captured, but an ultrasound image of a portion having a mammary gland region as the center may be captured. In this case, a mammary gland region is specified from the radiographic image captured by the radiation detector 30. However, in some cases, it is difficult to determine which position on the compression plate 34 the region specified as the mammary gland region in the radiographic image corresponds to.

Figure 4B:
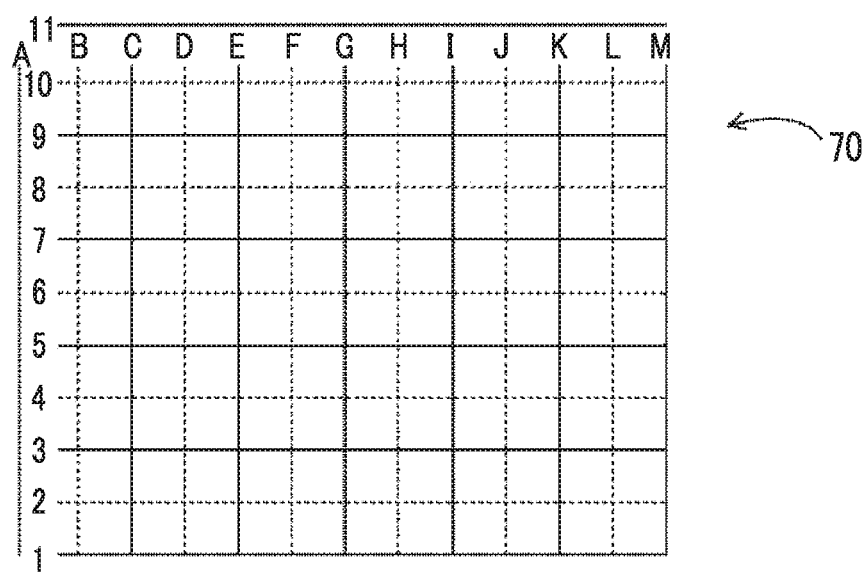
FIG. 4B is a diagram illustrating an example of a compression plate scale.

Therefore, for, as illustrated in FIG. 4A, the compression plate scale 70 whose example is illustrated in FIG. 4B is provided on the upper surface 34A of the compression plate 34 according to this embodiment. As illustrated in FIGS. 4A and 4B, the compression plate scale 70 according to this embodiment includes a plurality of grid-shaped lines including solid lines and dotted lines and symbols for identifying each of the plurality of lines. Specifically, the compression plate scale 70 includes 13 vertical lines and alphabets A to M are given to the vertical lines in order from the left side of the subject. The compression plate scale 70 includes 11 horizontal lines and numbers 1 to 11 are given to the horizontal lines in order from the chest wall of the subject. In the radiography system 2 according to this embodiment, a position on the upper surface 34A of the compression plate 34 is specified by a combination of the alphabet indicating the vertical line and the number indicating the horizontal line.

The compression plate scale 70 is not included in the radiographic image captured by the radiation detector 30. In other words, the captured radiographic image does not include an image indicating the compression plate scale 70. For example, carbon (C) can be used as the material forming the compression plate scale 70. In addition, it is preferable that the plurality of grid-shaped lines are thin lines and symbols are configured to have a small size in order to prevent the compression plate scale 70 from being included in the radiographic image.

In this embodiment, the aspect in which the compression plate scale 70 is provided on the upper surface 34A of the compression plate 34 has been described. However, the position where the compression plate scale 70 is provided is not limited to the upper surface 34A. For example, the compression plate scale 70 may be provided on a lower surface 34D of the compression plate 34 which faces the imaging table 40, that is, the lower surface 34D which comes into contact with the breast or may be provided on any one of the upper surface 34A, the lower surface 34D, or a surface which is parallel to the upper surface 34A between the upper surface 34A and the lower surface 34D of the compression plate 34. The lower surface 34D according to this embodiment is an example of a second surface according to the present disclosure and the surface parallel to the upper surface 34A according to this embodiment is an example of a third surface according to the present disclosure. As such, the second surface according to the present disclosure is a surface (the lower surface 34D in this embodiment) of the compression plate 34 which comes into contact with the breast, that is, a surface of the compression plate 34 which is farther from the radiation source 36R. Further, the third surface according to the present disclosure is a cross section of the compression plate 34 which is parallel to the first surface and is a surface which is present in the compression plate 34.

The compression plate 34 provided in the mammography apparatus 10 according to this embodiment is not limited to the compression plate illustrated in FIG. 4A and a plurality of types of compression plates 34 may be provided. In this example, the compression plate 34 compresses the entire breast. However, the present disclosure is not limited thereto. For example, a compression plate 34 that compresses a part of the breast may be used. In other words, the compression plate 34 may be smaller than the breast. For example, as the compression plate 34, a compression plate 34 used for so-called spot imaging which captures a radiographic image of only a region in which a lesion exists is known.

Further, other types of compression plates 34 include, for example, a compression plate corresponding to the size of the breast, a compression plate for axillary imaging, and a compression plate for enlarged imaging. In the radiography system 2 according to this embodiment, in some cases, the compression plate scale 70 varies depending on the type of the compression plate 34. For example, the size of the grid of the compression plate scale 70 may be different, the shape of the grid may be different, and the symbol corresponding to each line may be different.

The console 12 according to this embodiment has a function of controlling the mammography apparatus 10 using, for example, an imaging order and various kinds of information acquired from a radiology information system (RIS) 5 through a wireless communication local area network (LAN) and commands input by the user through an operation unit 56.

For example, the console 12 according to this embodiment is a server computer. As illustrated in FIG. 2, the console 12 comprises a control unit 50, a storage unit 52, an I/F unit 54, the operation unit 56, and a display unit 58. The control unit 50, the storage unit 52, the I/F unit 54, operation unit 56, and the display unit 58 are connected to each other through a bus 59, such as a system bus or a control bus, such that they can transmit and receive various kinds of information. The display unit 58 according to this embodiment is an example of a display device according to the present disclosure.

The control unit 50 according to this embodiment controls the overall operation of the console 12. The control unit 50 comprises a CPU 50A, a ROM 50B, and a RAM 50C. For example, various programs including a display control processing program 51 (which will be described below) executed by the CPU 50A are stored in the ROM 50B in advance. The RAM 50C temporarily stores various kinds of data. The display control processing program 51 according to this embodiment is an example of a control program according to the present disclosure.

For example, the image data of the radiographic image captured by the mammography apparatus 10 and various other kinds of information are stored in the storage unit 52. An HDD or an SSD is given as an example of the storage unit 52. The storage unit 52 according to this embodiment stores image scale information 53.

In the console 12 according to this embodiment, in a case in which a radiographic image is displayed on the display unit 58, control is performed to display an image scale 72 (see FIG. 11) corresponding to the compression plate scale 70 of the compression plate 34 used for imaging on the radiographic image. The image scale 72 according to this embodiment is an example of second position identification information according to the present disclosure. As described above, in some cases, there are a plurality of types of compression plates 34 and the compression plate scale 70 varies depending on the type of compression plate. Therefore, in this embodiment, the image scales 72 to be displayed are associated with each type of compression plate 34 in advance. The image scale information 53 indicates the correspondence relationship between the type of compression plate 34 and information indicating the image scale 72 to be displayed. FIG. 5A illustrates an example of the image scale information 53 according to this embodiment. The image scale information 53 illustrated in FIG. 5A indicates the correspondence relationship between a compression plate identification (ID) indicating the type of compression plate and an image scale ID indicating the image scale 72. According to the image scale information 53 illustrated in FIG. 5A, for example, the image scale 72 with an image scale ID "S0021" is associated with the compression plate 34 with a compression plate ID "B0021". In addition, as illustrated in FIG. 5A, the image scale ID is not associated with the compression plate 34 with a compression plate ID "B0010" (see "None" in FIG. 5A). This indicates that the compression plate scale 70 is not given to the type of compression plate 34 indicated by the compression plate ID "B0010" and thus there is no corresponding image scale 72. As such, in some cases, the mammography apparatus 10 according to this embodiment is provided with the compression plate 34 without the compression plate scale 70.

Further, in the mammography apparatus 10 according to this embodiment, the position of the compression plate 34 with respect to the imaging table 40 is different between the CC imaging and the MLO imaging. Therefore, even in a case in which the same type of compression plate 34 is used, an image scale 72 corresponding to a radiographic image captured by the CC imaging may be different from an image scale 72 corresponding to a radiographic image captured by the MLO imaging. For example, in the image scale information 53 illustrated in FIG. 5A, even in a case in which the types of imaging are different from each other, the types of compression plate 34 are regarded as being different from each other. In other words, in this embodiment, the type of compression plate 34 also includes the type of imaging. For example, in FIG. 5A, the compression plate 34 with the compression plate ID "B0021" indicates the compression plate 34 in a case in which the CC imaging is performed and a compression plate 34 with a compression plate ID "B0022" indicates a compression plate 34 in a case in which an image of the right breast of the subject is captured by the MLO imaging using the compression plate 34 with the compression plate ID "B0021". A compression plate 34 with a compression plate ID "B0023" indicates a compression plate 34 in a case in which an image of the left breast of the subject is captured by the MLO imaging using the compression plate 34 with the compression plate ID "B0021". In this embodiment, the CC imaging and the MLO imaging are given as examples of the type of imaging. However, the types of imaging are not limited thereto. For example, tomosynthesis imaging may be included as the type of imaging.

Unlike the image scale information 53 according to this embodiment, the type of imaging may not be included in the type of the compression plate 34. FIG. 5B illustrates an example of the image scale information 53 in this case. The image scale information 53 illustrated in FIG. 5B indicates the correspondence relationship among the compression plate ID indicating the type of the compression plate 34, the type of imaging, and the image scale ID indicating the image scale 72. According to the image scale information 53 illustrated in FIG. 5B, for example, an image scale 72 with an image scale ID "S0021" is associated with the compression plate 34 with the compression plate ID "B0020" and the CC imaging indicating that the type of imaging is CC. For example, an image scale 72 with an image scale ID "S0022" is associated with the compression plate 34 with the compression plate ID "B0020" and right breast MLO imaging indicating that the type of imaging is "MLO (right)".

Figures 5C, 6:
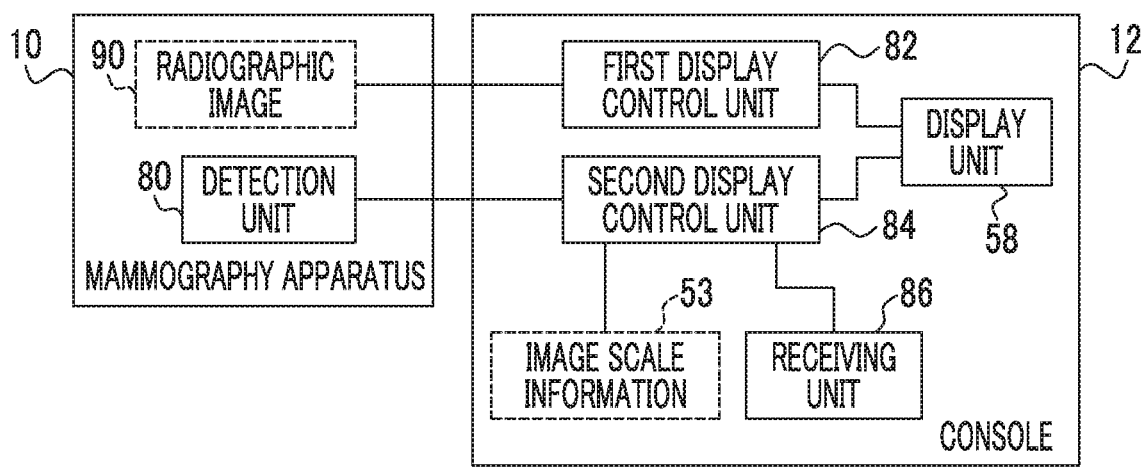
FIG. 5C is a diagram illustrating still another example of the image scale information according to the first embodiment.
FIG. 6 is a functional block diagram illustrating an example of the function of a mammography apparatus and a console according to the first embodiment.

The image scale information 53 is not limited to the image scale information 53 illustrated in FIG. 5A and the image scale information 53 illustrated in FIG. 5B. For example, FIG. 5C illustrates image scale information 53 indicating the correspondence relationship among the compression plate ID, information indicating the irradiation field, and the image scale ID. In the mammography apparatus 10 according to this embodiment, the size and position of the irradiation field of the radiation R emitted from the radiation source 36R are determined by a collimator (not illustrated). Since the radiographic image to be captured changes depending on the size and position of the irradiation field, the image scale 72 to be displayed on the radiographic image also changes. In this case, it is preferable to use information indicating the irradiation field as one of parameters for specifying the image scale 72 to be displayed on the radiographic image. The image scale information 53 illustrated in FIG. 5C is information indicating the correspondence relationship in which the irradiation field is further added as the parameter for specifying the image scale 72, as compared to the image scale information 53 illustrated in FIG. 5A.

The operation unit 56 is used by the user to input, for example, commands which are related to the capture of a radiographic image and include a command to emit the radiation R or various kinds of information. Therefore, the operation unit 56 according to this embodiment includes at least an irradiation command button that is pressed by the user to input a command to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS 5, and the image storage system 18 using wireless communication or wired communication. In the radiography system 2 according to this embodiment, the console 12 receives the image data of the radiographic image captured by the mammography apparatus 10 from the mammography apparatus 10 through the I/F unit 54, using wireless communication or wired communication.

FIG. 6 is a functional block diagram illustrating an example of the configuration of the mammography apparatus 10 and the console 12 according to this embodiment. As illustrated in FIG. 6, the mammography apparatus 10 according to this embodiment comprises a detection unit 80. For example, in the mammography apparatus 10 according to this embodiment, the CPU 20A of the control unit 20 executes the imaging processing program 21 stored in the ROM 20B such that the control unit 20 functions as the detection unit 80.

The detection unit 80 of the mammography apparatus 10 detects the type of the compression plate 34 attached to the mammography apparatus 10 on the basis of the compression plate identifier provided on the surface 34C of the compression plate 34 which has been read by the compression plate detection sensor 35 and outputs the detection result to the console 12.

The console 12 according to this embodiment comprises a first display control unit 82, a second display control unit 84, and a receiving unit 86. For example, in the console 12 according to this embodiment, the CPU 50A of the control unit 50 executes the display control processing program 51 stored in the ROM 50B such that the control unit 50 functions as the first display control unit 82, the second display control unit 84, and the receiving unit 86.

Image data of a radiographic image 90 captured by the mammography apparatus 10 is input to the first display control unit 82. The first display control unit 82 performs control to display the radiographic image 90 indicated by the input image data on the display unit 58.

The detection result is input to the second display control unit 84 from the detection unit 80 of the mammography apparatus 10. The second display control unit 84 specifies the image scale 72 corresponding to the type of the compression plate 34 indicated by the detection result with reference to the image scale information 53. Further, the second display control unit 84 performs control to display the specified image scale 72 on the radiographic image 90 displayed on the display unit 58 by the first display control unit 82.

The receiving unit 86 receives various types of designation performed by the user on the radiographic image 90 displayed on the display unit 58. For example, in this embodiment, whether the image scale 72 is to be displayed or not to be displayed on the radiographic image 90 displayed on the display unit 58 is received. In this embodiment, the display of the image scale 72 on the display unit 58 is referred to as the turn-on of the image scale 72 and the non-display of the image scale 72 is referred to as the turn-off of the image scale 72.

Figure 7:
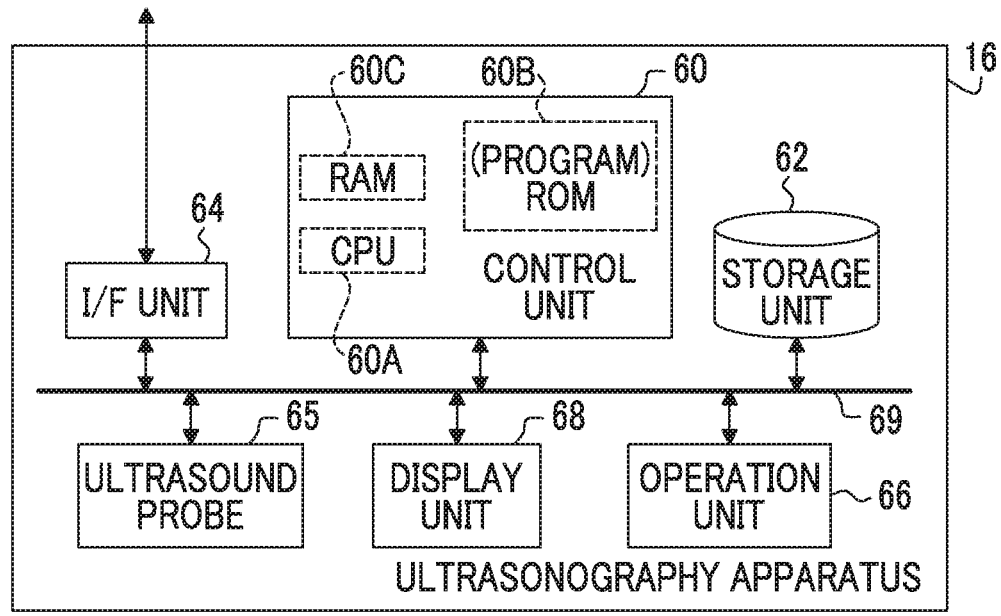
FIG. 7 is a block diagram illustrating an example of the configuration of an ultrasonography apparatus according to the first embodiment.

Next, the configuration of the ultrasonography apparatus 16 will be described. FIG. 7 is a block diagram illustrating an example of the configuration of the ultrasonography apparatus 16. The ultrasonography apparatus 16 is used by the user to capture an ultrasound image of the breast of the subject as the object and is a so-called hand-held ultrasonography apparatus.

As illustrated in FIG. 7, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, such that they can transmit and receive various kinds of information.

The control unit 60 according to this embodiment controls the overall operation of the ultrasonography apparatus 16. The control unit 60 comprises a CPU 60A, a ROM 60B, and a RAM 60C. For example, various programs executed by the CPU 60A are stored in the ROM 60B in advance. The RAM 60C temporarily stores various kinds of data.

For example, the image data of the captured ultrasound image and various other kinds of information are stored in the storage unit 62. A specific example of the storage unit 62 is an HDD or an SSD.

The ultrasound probe 65 is moved along the upper surface 34A (see FIG. 3, a surface opposite to the surface that comes into contact with the breast of the subject) of the compression plate 34 by the user and scans the breast with ultrasonic waves to acquire an ultrasound image of the breast. Specifically, in a case in which ultrasonography is performed, the ultrasound probe 65 is moved by the user along the upper surface 34A of the compression plate 34 in a state in which an acoustic matching member (not illustrated), such as echo jelly, is applied onto the upper surface 34A of the compression plate 34. In this embodiment, since the compression plate scale 70 is provided on the upper surface 34A of the compression plate 34 as described above, the user can move the ultrasound probe 65 while checking the position of the mammary gland region using the compression plate scale 70.

The ultrasound probe 65 comprises a plurality of ultrasound transducers (not illustrated) which are one-dimensionally or two-dimensionally arranged. Each of the ultrasound transducers transmits ultrasonic waves on the basis of an applied driving signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electric signal. The electric signal is output as an ultrasound received signal and is input to the main body (not illustrated) of the ultrasonography apparatus 16 through a cable (not illustrated).

The operation unit 66 is used by the user to input, for example, commands or various kinds of information related to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 transmits and receives various kinds of information to and from the RIS 5 and the image storage system 18 using wireless communication or wired communication. The image data of the ultrasound image captured by the ultrasonography apparatus 16 is transmitted to the image storage system 18 through the I/F unit 64 by wireless communication or wired communication.

Figure 8:
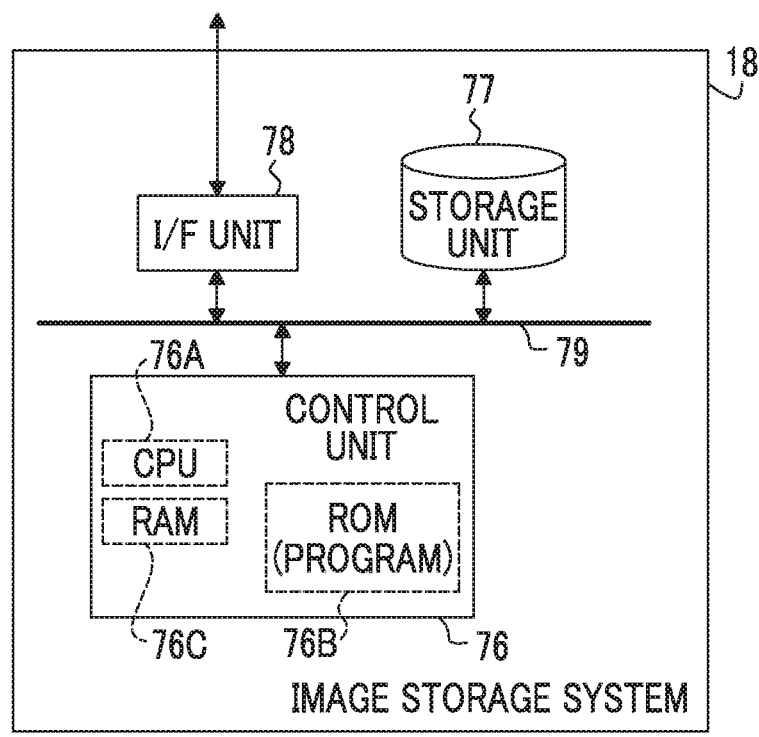
FIG. 8 is a block diagram illustrating an example of the configuration of an image storage system according to the first embodiment.

Next, the configuration of the image storage system 18 will be described. FIG. 8 is a block diagram illustrating an example of the configuration of the image storage system 18. The image storage system 18 stores the image data of the radiographic image captured by the radiography system 2 and the image data of the ultrasound image captured by the ultrasonography apparatus 16. The image storage system 18 extracts an image corresponding to a request from, for example, the console 12, the ultrasonography apparatus 16, and other reading devices (not illustrated) from the stored radiographic images and ultrasound images and transmits the extracted image to the apparatus which is the request source. A specific example of the image storage system 18 is a picture archiving and communication system (PACS).

As illustrated in FIG. 8, the image storage system 18 comprises a control unit 76, a storage unit 77, and an I/F unit 78. The control unit 76, the storage unit 77, and the I/F unit 78 are connected to each other through a bus 79, such as a system bus or a control bus, such that they can transmit and receive various kinds of information.

The control unit 76 according to this embodiment controls the overall operation of the ultrasonography apparatus 16. The control unit 76 comprises a CPU 76A, a ROM 76B, and a RAM 76C. For example, various programs executed by the CPU 76A are stored in the ROM 76B in advance. The RAM 76C temporarily stores various kinds of data.

The storage unit 77 is a so-called database that stores each of the image data of the radiographic image and the image data of the ultrasound image so as to be associated with, for example, an imaging order or information released to the subject.

The I/F unit 78 has a function of transmitting and receiving various kinds of information to and from the console 12 and the ultrasonography apparatus 16 using wireless communication or wired communication.

Next, the operation of the console 12 according to this embodiment will be described with reference to the drawings.

Figure 9:
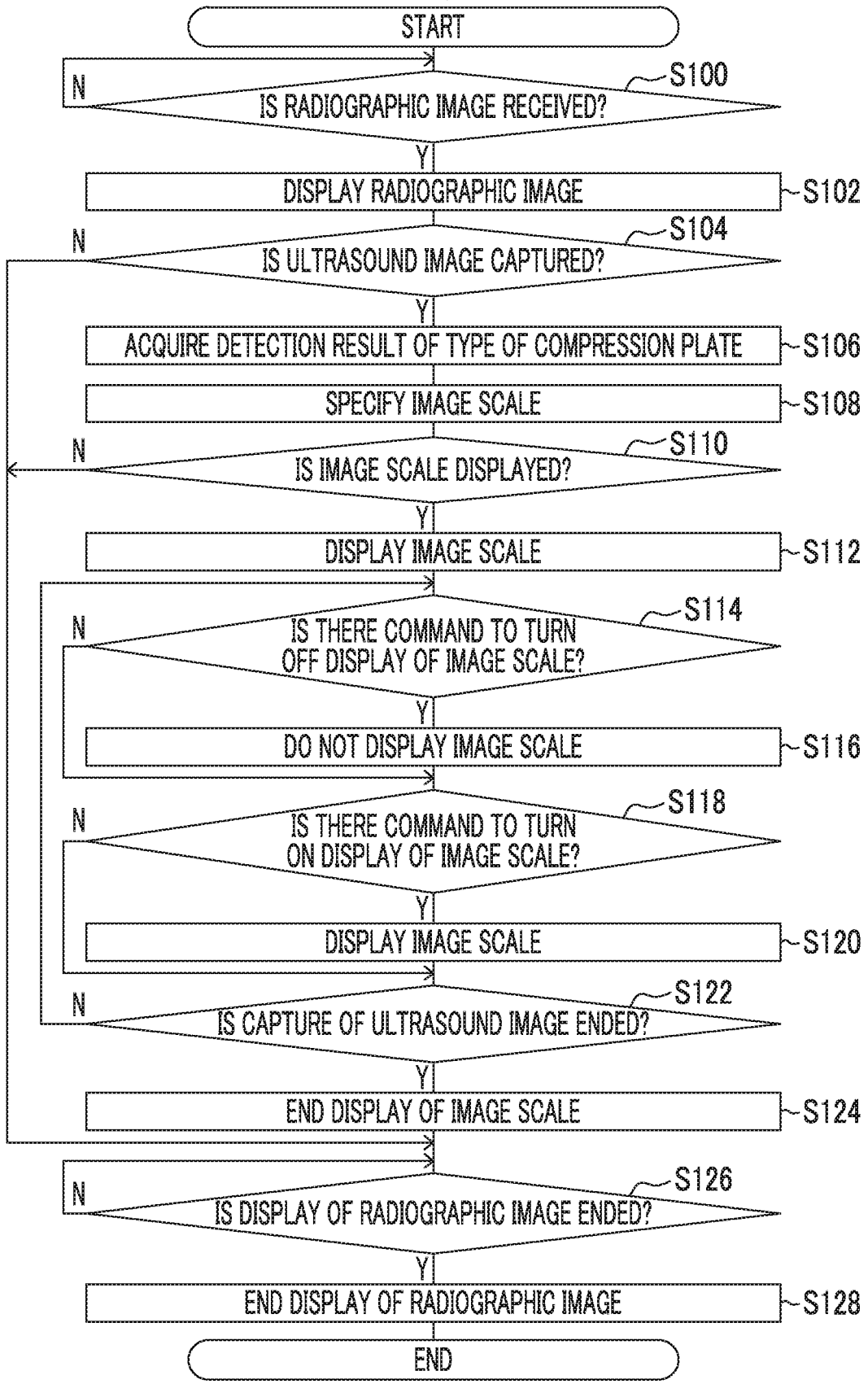
FIG. 9 is a flowchart illustrating an example of the flow of a display control process of the console according to the first embodiment.

For example, in a case in which the console 12 according to this embodiment receives an imaging start command corresponding to an imaging order designated by the user through the operation unit 56, the CPU 50A of the control unit 50 executes the display control processing program 51 stored in the ROM 50B to perform a display control process whose example is illustrated in FIG. 9. FIG. 9 is a flowchart illustrating an example of the flow of a display control operation of the console 12 according to this embodiment.

In a case in which a radiographic image is captured by the mammography apparatus 10 according to this embodiment, the control unit 20 of the mammography apparatus 10 places the radiation source 36R and the imaging table 40 at an imaging position corresponding to the type of imaging used to capture the radiographic image. Specifically, the control unit 20 places the radiation source 36R and the imaging table 40 at an imaging position in one of the CC imaging, the MLO imaging for the left chest of the subject, and the MLO imaging for the right chest of the subject according to an imaging menu.

In a case in which the imaging table 40 and the radiation source 36R of the mammography apparatus 10 are located at the imaging position, the user positions the breast of the subject on the imaging surface 40A of the imaging table 40. In a case in which the positioning is completed, the user inputs a compression command through the operation unit 26. In response to the compression command, the compression plate driving unit 32 moves the compression plate 34 in the compression direction and the compression plate 34 compresses the breast between the compression plate 34 and the imaging surface 40A of the imaging table 40.

The compression of the breast by the compression plate 34 makes it possible to develop the overlap between the mammary gland tissues and to easily determine whether a lesion is a benign lesion or a malignant lesion. In addition, since the breast is compressed and fixed to the imaging table 40 by the compression plate 34, the body movement of the subject is suppressed. Therefore, it is possible to suppress the blurring of a radiographic image caused by the body movement. Further, since the breast is compressed by the compression plate 34, the thickness of the breast is reduced. Therefore, it is possible to reduce the amount of radiation emitted to the breast.

In a case in which the breast is fixed by the compression plate 34, the user presses an irradiation command button included in the operation unit 56 of the console 12 to input a command to emit the radiation R. In a case in which the irradiation command is input, the control unit 20 of the mammography apparatus 10 performs control such that the radiation R is emitted from the radiation source 36R to the breast compressed by the compression plate 34 under the control of the console 12. Then, the radiation detector 30 generates a radiographic image on the basis of the radiation R transmitted through the breast. The image data of the captured radiographic image is transmitted to the console 12.

In the display control process illustrated in FIG. 9, first, in Step S100, the first display control unit 82 determines whether or not the image data of the radiographic image 90 has been received from the mammography apparatus 10. The determination result in Step S100 is "No" until the image data of the radiographic image 90 is received from the mammography apparatus 10. On the other hand, in a case in which the image data of the radiographic image 90 has been received from the mammography apparatus 10, the determination result in Step S100 is "Yes" and the process proceeds to Step S102.

Figure 10:
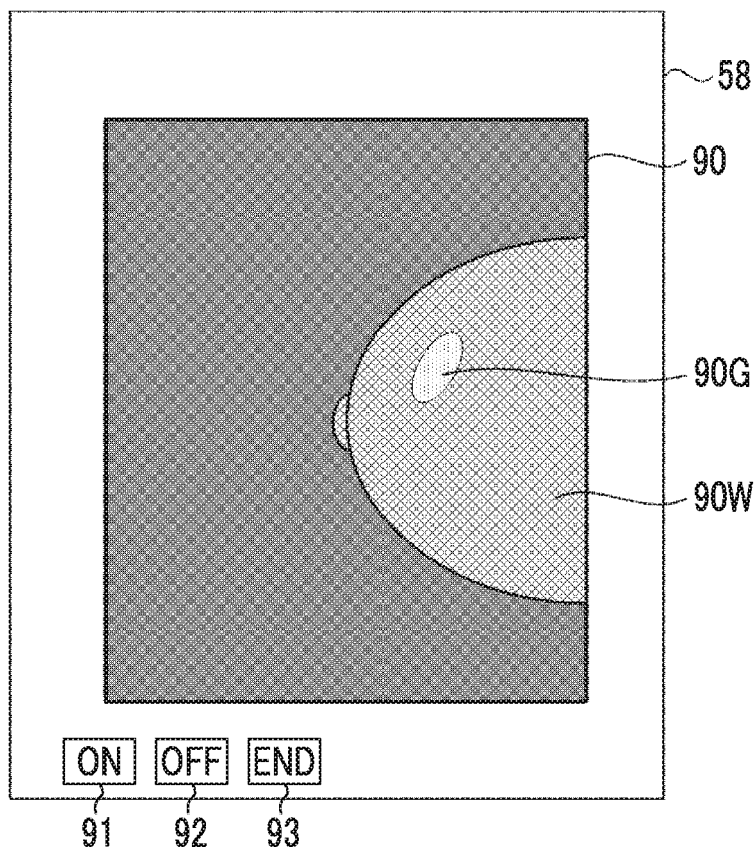
FIG. 10 is a diagram illustrating an example of a radiographic image displayed on a display unit according to the first embodiment.

In Step S102, the first display control unit 82 performs control to display the radiographic image 90 indicated by the received image data on the display unit 58. FIG. 10 illustrates an example of the radiographic image 90 displayed on the display unit 58. The radiographic image 90 illustrated in FIG. 10 includes a breast image 90W corresponding to the breast of the subject and the breast image 90W includes a mammary gland image 90G corresponding to the mammary gland.

As illustrated in FIG. 10, the first display control unit 82 according to this embodiment further displays an on button 91, an off button 92, and an end button 93 on the display unit 58. The on button 91 is a button operated by the user to display the image scale 72. The off button 92 is a button operated by the user to remove the displayed image scale 72. The end button 93 is a button operated by the user to end the display of the radiographic image 90. In this embodiment, for example, for the "display" of the radiographic image 90, switching from a display state to a non-display state is referred to as "end". For example, the switching means removing the radiographic image 90 displayed on the display unit 58 from the display unit 58.

In Step S104, the second display control unit 84 determines whether or not to capture an ultrasound image. In other words, the second display control unit 84 determines whether or not to perform continuous imaging that continuously captures an ultrasound image while maintaining the compressed state of the breast by the compression plate 34 after the radiographic image is captured. For example, in a case in which a command to capture both a radiographic image and an ultrasound image is included in the imaging order or the user inputs a command to capture an ultrasound image through the operation unit 56, the second display control unit 84 according to this embodiment determines to capture an ultrasound image.

In a case in which an ultrasound image is not captured, the determination result in Step S104 is "No" and the process proceeds to Step S126. On the other hand, in a case in which an ultrasound image is captured, the determination result in Step S104 is "Yes" and the process proceeds to Step S106.

In Step S106, the second display control unit 84 acquires the detection result of the type of the compression plate 34 from the detection unit 80 of the mammography apparatus 10.

Figure 11:
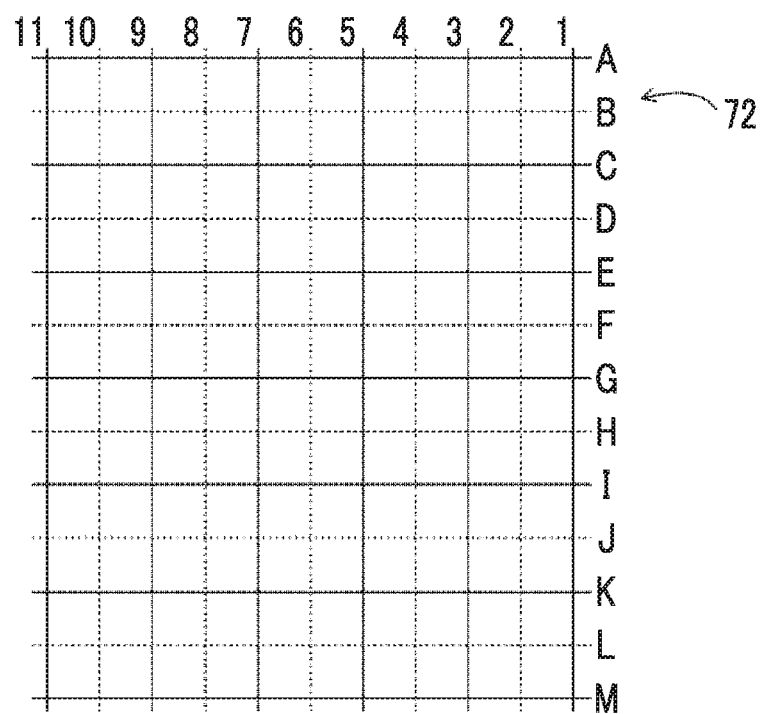
FIG. 11 is a diagram illustrating an example of an image scale according to the first embodiment.

Then, in Step S108, the second display control unit 84 specifies an image scale 72 that is associated with the compression plate ID corresponding to the type of the compression plate 34 indicated by the detection result acquired in Step S106, with reference to the image scale information 53 (see FIG. 5A) stored in the storage unit 52. FIG. 11 illustrates an example of the image scale 72 specified by the second display control unit 84. The image scale 72 illustrated in FIG. 11 includes a plurality of grid-shaped lines including solid lines and dotted lines and symbols for identifying each of the plurality of lines, similarly to the compression plate scale 70 (see FIG. 4B). Specifically, the image scale 72 includes 13 horizontal lines and alphabets A to M are given to the horizontal lines. The image scale 72 includes 11 vertical lines and numbers 1 to 11 are given to the vertical lines. In the radiography system 2 according to this embodiment, a position on the radiographic image 90 is specified by a combination of an alphabet indicating a horizontal line and a number indicating a vertical line.

As described above, in the case of the type of compression plate 34 without the compression plate scale 70, the image scale ID is not associated with the compression plate ID of the image scale information 53. For example, according to the image scale information 53 illustrated in FIG. 5A, in a case in which the compression plate ID is "B0010", the image scale ID is not associated. In this case, the second display control unit 84 specifies that the image scale 72 is not displayed.

Then, in Step S110, the second display control unit 84 determines whether or not to display the image scale 72. Specifically, the second display control unit 84 determines whether or not the image scale 72 has been specified not to be displayed in Step S108. In a case in which the image scale 72 is not displayed, the determination result in Step S110 is "No" and the process proceeds to Step S126. On the other hand, in a case in which the image scale 72 is displayed, the determination result in Step S110 is "Yes" and the process proceeds to Step S112.

Figure 12:
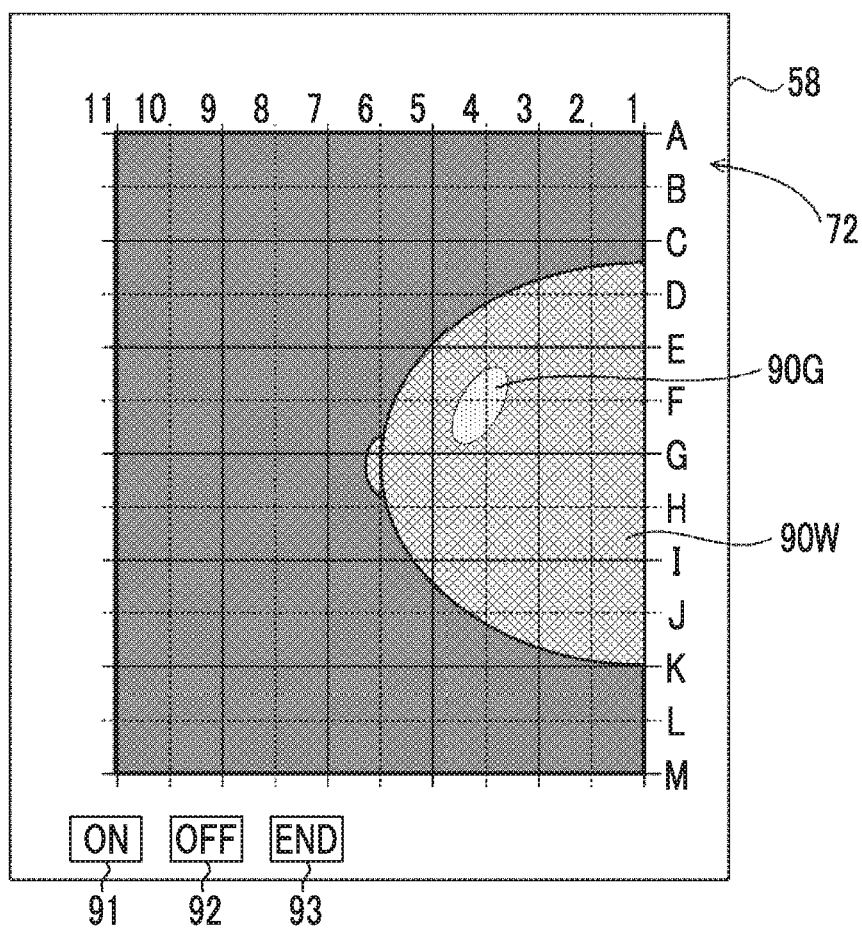
FIG. 12 is a diagram illustrating an example of the image scale that is displayed on the radiographic image displayed on the display unit according to the first embodiment.

In Step S112, the second display control unit 84 performs control to display the image scale 72 specified in Step S108 on the radiographic image 90 displayed on the display unit 58. FIG. 12 illustrates an example of a state in which the image scale 72 illustrated in FIG. 11 is displayed on the radiographic image 90 displayed on the display unit 58.

Then, in Step S114, the second display control unit 84 determines whether or not the receiving unit 86 has received a command to turn off the display of the image scale 72. In this embodiment, in a case in which the off button 92 displayed on the display unit 58 has not been operated by the user, the determination result in Step S114 is "No" and the process proceeds to Step S118. On the other hand, in a case in which the off button 92 has been operated by the user, the determination result in Step S114 is "Yes" and the process proceeds to Step S116.

In Step S116, the second display control unit 84 performs control to remove the image scale 72 displayed on the display unit 58. The display state of the radiographic image 90 and the image scale 72 on the display unit 58 is changed from the state illustrated in FIG. 12 to the state illustrated in FIG. 10 by this control.

Then, in Step S118, the second display control unit 84 determines whether or not the receiving unit 86 has received a command to turn on the display of the image scale 72. In this embodiment, in a case in which the on button 91 displayed on the display unit 58 has not been operated by the user, the determination result in Step S118 is "No" and the process proceeds to Step S122. On the other hand, in a case in which the on button 91 has been operated by the user, the determination result in Step S118 is "Yes" and the process proceeds to Step S120.

In Step S120, the second display control unit 84 performs control to display the image scale 72 on the radiographic image 90 displayed on the display unit 58. The display state of the radiographic image 90 and the image scale 72 on the display unit 58 is changed from the state illustrated in FIG. 10 to the state illustrated in FIG. 12 by this control.

Since the image scale 72 is displayed on the radiographic image 90 displayed on the display unit 58, the user can identify the position of the mammary gland image 90G using the image scale 72. For example, in the example illustrated in FIG. 12, the position of the mammary gland image 90G can be identified as the position of "F4" where the line F and the line 4 of the image scale 72 intersect each other. A method for specifying the position of the mammary gland image 90G is not limited to the method for specifying the position where the horizontal line (lines A to M) and the vertical line (lines 1 to 11) of the image scale 72 intersect each other. For example, a method may be used which specifies the position using the lines of the image scale 72 surrounding the mammary gland image 90G. For example, in the case of the mammary gland image 90G illustrated in FIG. 12, a position within a region that is surrounded by the line E, the line G, the line 3, and the line 5 of the image scale 72 may be specified as the position of the mammary gland image 90G. In this case, for example, even in a case in which the mammary gland image 90G is small and is not placed across an intersection portion of the lines for specifying a position on the image scale 72, it is possible to appropriately specify the position of the mammary gland image 90G.

Further, a method may be used which specifies, as the position of the mammary gland image 90G, the position of a grid which includes the mammary gland image 90G among a plurality of grids formed by a plurality of lines. For example, in the case of the mammary gland image 90G illustrated in FIG. 12, the positions of four grids, specifically, a grid formed by the line E, the line F, the line 3, and the line 4, a grid formed by the line E, the line F, the line 4, and the line 5, a grid formed by the line F, the line G, the line 3, and the line 4, and a grid formed by the line F, the line G, the line 4, and the line 5 may be specified as the position of the mammary gland image 90G. In this case, a grid in which the ratio of the size (area) of the mammary gland image 90G included in the grid to the area of the grid is equal to or greater than a predetermined value may be regarded as the grid including the mammary gland image 90G.

The user uses the ultrasonography apparatus 16 to take an ultrasound image of the breast compressed by the compression plate 34 on the basis of the position of the mammary gland 90G specified by the image scale 72. Specifically, the user applies an acoustic matching member (not illustrated), such as echo jelly, onto the upper surface 34A of the compression plate 34. The user operates the ultrasound probe 65 to scan the upper surface 34A of the compression plate 34 covered by the acoustic matching member with ultrasonic waves, thereby capturing an ultrasound image. The captured ultrasound image is displayed on the display unit 68 of the ultrasonography apparatus 16.

In a case in which the continuous imaging is performed, the compressed state of the breast may not be completely the same between the state in which the radiographic image is captured and the state in which the ultrasound image is captured. For example, the compression force or compression pressure of the compression plate 34 against the breast may be changed. As described above, the overlap of the mammary gland tissues is developed by the compression of the breast by the compression plate 34. Therefore, it is possible to change the compression force or the compression pressure to the extent that the overlap of the mammary gland tissues, that is, the development of the mammary gland tissues is not changed or the amount of change is within an allowable range even in a case in which the overlap is changed. For example, as the compressed state of the breast for the time from the start of the capture of a radiographic image to the end of the capture of an ultrasound image, the breast may be continuously compressed to the extent that the area of the breast which comes into contact with the imaging surface 40A of the imaging table 40 is not changed. Therefore, the mammography apparatus 10 may reduce the compression against the breast according to the area of the breast which comes into contact with the imaging surface 40A after a radiographic image is captured and before an ultrasound image is captured.

Then, in Step S122, the second display control unit 84 determines whether the capture of an ultrasound image has ended. For example, in this embodiment, in a case in which the capture of an ultrasound image ends, the user inputs a command to release the compression through the operation unit 26 of the mammography apparatus 10. In a case in which the command to release the compression has been input through the operation unit 26, the second display control unit 84 according to this embodiment determines that the capture of an ultrasound image has ended.

In a case in which the capture of an ultrasound image has not ended, that is, in a case in which the command to release the compression has not been input, the determination result in Step S122 is "No" and the process returns to Step S114. Then, the process in Steps S116 to S120 is repeated. On the other hand, in a case in which the capture of an ultrasound image has ended, that is, in a case in which the command to release the compression has been input, the determination result in Step S122 is "Yes" and the process proceeds to Step S124.

In Step S124, the second display control unit 84 ends the display of the image scale 72 on the radiographic image 90 displayed on the display unit 58. The display state of the radiographic image 90 and the image scale 72 on the display unit 58 is changed from the state illustrated in FIG. 12 to the state illustrated in FIG. 10 by this process.

Then, in Step S126, the first display control unit 82 determines whether or not to end the display of the radiographic image 90. In this embodiment, in a case in which the end button 93 displayed on the display unit 58 has not been operated by the user, the determination result in Step S126 is "No". On the other hand, in a case in which the end button 93 has been operated by the user, the determination result in Step S126 is "Yes" and the process proceeds to Step S128.

In a case in which the first display control unit 82 ends the display of the radiographic image 90 in Step S128, the display control process ends.

A method for determining whether or not to capture an ultrasound image in Step S104 of the display control process in the second display control unit 84 is not limited to the above-mentioned method. For example, methods according to the following Modification Examples 1 to 3 may be applied.

Modification Example 1

The second display control unit 84 may determine whether or not to capture an ultrasound image on the basis of the amount of mammary gland in the breast as the object. In many cases, the capture of an ultrasound image is performed in a mammary gland region in which mammary gland tissues are likely to overlap each other. Therefore, an ultrasound image can be captured in a case in which the amount of mammary gland is relatively large.

Figure 13:
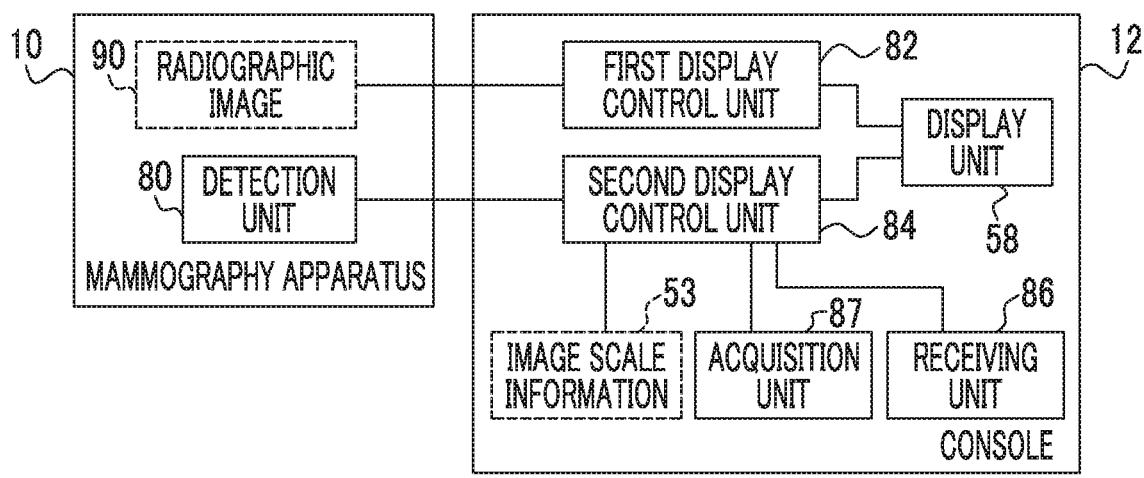
FIG. 13 is a functional block diagram illustrating an example of the function of mammography apparatuses and consoles according to Modification Examples 1 and 2.

FIG. 13 is a functional block diagram illustrating an example of the configuration of a mammography apparatus 10 and a console 12 according to this modification example. The console 12 illustrated in FIG. 13 is different from the console 12 illustrated in FIG. 6 in that it further comprises an acquisition unit 87. For example, in the console 12 according to this modification example, the CPU 50A of the control unit 50 executes the display control processing program 51 stored in the ROM 50B such that the control unit 50 functions as the acquisition unit 87.

The acquisition unit 87 acquires mammary gland amount information indicating the amount of mammary gland from the radiographic image captured by the radiation detector 30 and outputs the acquired mammary gland amount information to the second display control unit 84. In addition, for example, the amount of mammary gland may be derived from the radiographic image by the acquisition unit 87 or the mammography apparatus 10. A method for deriving the amount of mammary gland in the breast is not particularly limited. For example, a known method, such as a technique that estimates a mammary gland content on the basis of a radiographic image and a fat image estimated from the radiographic image described in JP2010-253245A, may be used as the method for deriving the amount of mammary gland from the radiographic image.

The second display control unit 84 receives the mammary gland amount information from the acquisition unit 87. The second display control unit 84 determines whether or not to capture an ultrasound image on the basis of the input mammary gland amount information. For example, in this modification example, in a case in which the amount of mammary gland indicated by the mammary gland amount information is equal to or greater than a mammary gland amount threshold value, an ultrasound image is captured since the amount of mammary gland is large. Further, for example, the mammary gland amount threshold value used for the determination by the second display control unit 84 may be experimentally obtained in advance. For example, the mammary gland amount threshold value may vary depending on the thickness of the breast.

Figure 14:
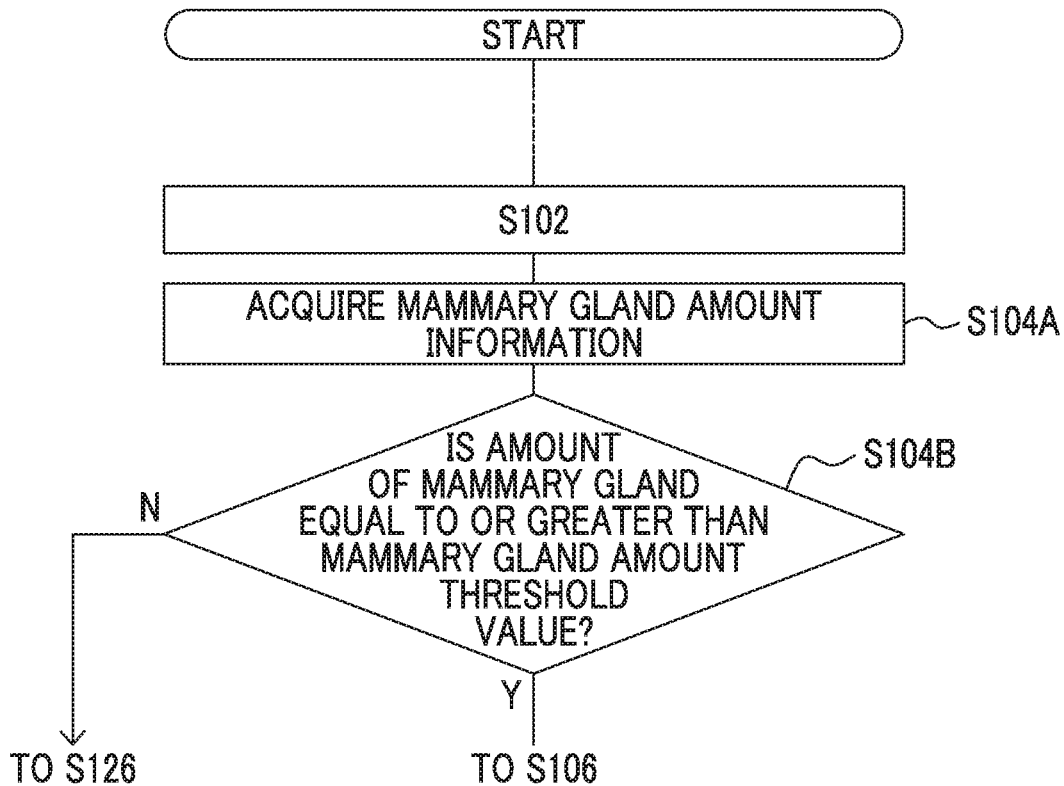
FIG. 14 is a flowchart illustrating an example of the flow of a display control process of the console according to Modification Example 1.

FIG. 14 illustrates a portion of a flowchart illustrating an example of the flow of a display control process of the console 12 according to this modification example. As illustrated in FIG. 14, the display control process according to this modification example is different from the display control process (see FIG. 9) according to this embodiment in that each process in Steps S104A and S104B is performed instead of Step S104.

In Step S104A of FIG. 14, the acquisition unit 87 acquires the mammary gland amount information and outputs the acquired mammary gland amount information to the second display control unit 84 as described above.

Then, in Step S104B, the second display control unit 84 determines whether or not the amount of mammary gland indicated by the mammary gland amount information is equal to or greater than the mammary gland amount threshold value. In a case in which the amount of mammary gland is equal to or greater than the mammary gland amount threshold value, the determination result in Step S104B is "Yes" and this corresponds to a case in which an ultrasound image is captured. Therefore, the process proceeds to Step S106 (see FIG. 9). On the other hand, in a case in which the amount of mammary gland is not equal to or greater than the mammary gland amount threshold value, that is, in a case in which the amount of mammary gland is less than the mammary gland amount threshold value, the determination result in Step S104B is "No" and this corresponds to a case in which an ultrasound image is not captured. Therefore, the process proceeds to Step S126 (see FIG. 9).

Modification Example 2

The second display control unit 84 may determine whether or not to capture an ultrasound image on the basis of a mammary gland region of the breast as the object. As the amount of mammary gland becomes larger, the size of the mammary gland region tends to become larger. As described in Modification Example 1, in many cases, the capture of an ultrasound image is performed for the mammary gland region in which the mammary gland tissues are likely to overlap each other. Therefore, an ultrasound image can be captured in a case in which the amount of mammary gland is relatively large.

The configuration of the console 12 according to this modification example further includes the acquisition unit 87, similarly to the console 12 according to Modification Example 1 (see FIG. 13).

The acquisition unit 87 acquires region information indicating the mammary gland region in the breast from the radiographic image captured by the radiation detector 30 and outputs the acquired region information to the second display control unit 84. The mammary gland region may be derived from the radiographic image by, for example, the acquisition unit 87 or the mammography apparatus 10. A method for deriving the mammary gland region is not particularly limited. For example, mammary gland tissue pixels corresponding to the mammary gland tissues can be detected from the radiographic image and a region in which the number of detected mammary gland tissue pixels is equal to or greater than a predetermined value can be derived as the mammary gland region. A method for detecting the mammary gland tissue pixel is not particularly limited. For example, a technique described in JP2010-253245A can be applied. In a case in which the technique described in this patent publication is applied, first, a radiographic image is divided into a breast image and a direct region and the pectoral muscle region is extracted in the breast image. Then, the pectoral muscle region is removed from the breast image. Then, in the breast image from which the pectoral muscle region has been removed, a pixel in which the amount of transmission of the radiation R is equal to or less than a threshold value is detected as the mammary gland tissue region pixel.

The second display control unit 84 receives the region information from the acquisition unit 87. The second display control unit 84 determines whether or not to capture an ultrasound image on the basis of the input region information. For example, in this modification example, in a case in which the size of the mammary gland region indicated by the region information is equal to or greater than a region threshold value, an ultrasound image is captured since the amount of mammary gland is large. Further, for example, the region threshold value used for the determination by the second display control unit 84 may be experimentally obtained in advance. In addition, for example, the region threshold value may vary depending on the thickness of the breast.

Figure 15:
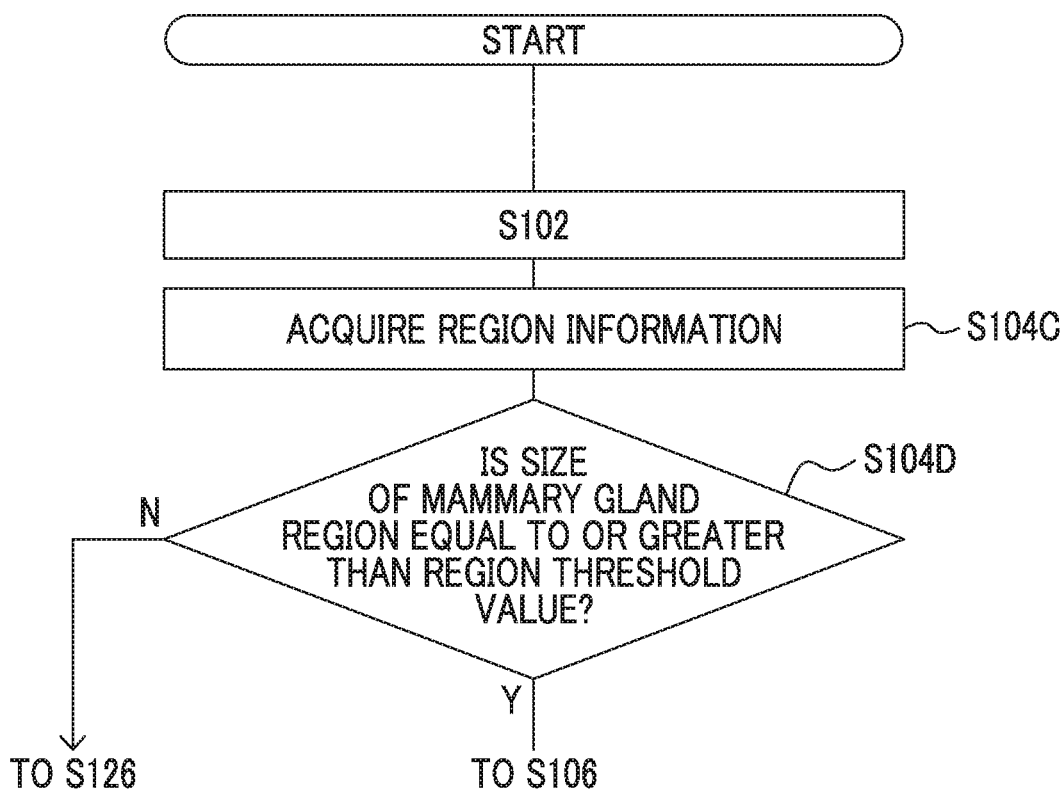
FIG. 15 is a flowchart illustrating an example of the flow of a display control process of the console according to Modification Example 2.

FIG. 15 illustrates a portion of a flowchart illustrating an example of the flow of a display control process of the console 12 according to this modification example. As illustrated in FIG. 15, the display control process according to this modification example is different from the display control process (see FIG. 9) according to this embodiment in that each process in Steps S104C and S104D is performed instead of Step S104.

In Step S104C of FIG. 15, the acquisition unit 87 acquires the region information and outputs the acquired region information to the second display control unit 84 as described above.

Then, in Step S104D, the second display control unit 84 determines whether or not the size of the mammary gland region indicated by the region information is equal to or greater than the region threshold value. In a case in which the size of the mammary gland region is equal to or greater than the region threshold value, the determination result in Step S104D is "Yes" and this corresponds a case in which an ultrasound image is captured. Therefore, the process proceeds to Step S106 (see FIG. 9). On the other hand, in a case in which the size of the mammary gland region is not equal to or greater than the region threshold value, that is, in a case in which the size of the mammary gland region is less than the region threshold value, the determination result in Step S104D is "No" and this corresponds a case in which an ultrasound image is not captured. Therefore, the process proceeds to Step S126 (see FIG. 9).

Modification Example 3

The second display control unit 84 may determine whether or not to capture an ultrasound image according to the time for which the compressed state of the breast is maintained by the compression plate 34 after a radiographic image is captured. In a case in which an ultrasound image is not captured after the radiographic image 90 is captured, the compression by the compression plate 34 is generally promptly released to reduce the burden on the subject after, for example, an imaging failure is checked in the captured radiographic image 90. On the other hand, in a case in which an ultrasound image is captured after the radiographic image 90 is captured, the process shifts to the capture of an ultrasound image after the radiographic image 90 is checked as described above. Therefore, the compression of the breast is maintained for a long time as compared to a case in which an ultrasound image is not captured. Therefore, a case in which the breast is kept pressed for a predetermined period of time or more after the radiographic image 90 is captured may be a case in which an ultrasound image is captured.

Since the configurations of the mammography apparatus 10 and the console 12 according to this modification example are the same as the configuration of the mammography apparatus 10 and the console 12 according to this embodiment (see FIG. 6), the description thereof will not be repeated.

Figure 16:
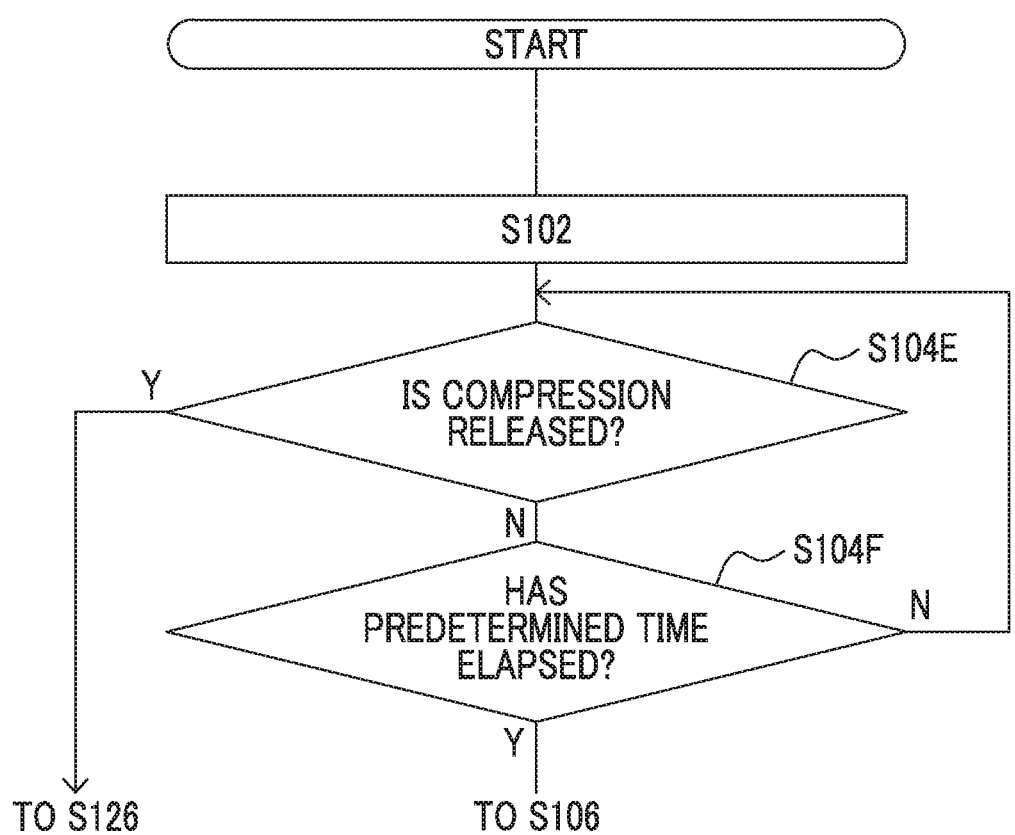
FIG. 16 is a flowchart illustrating an example of the flow of a display control process of a console according to Modification Examples 3.

FIG. 16 illustrates a portion of a flowchart illustrating an example of the flow of a display control process of the console 12 according to this modification example. As illustrated in FIG. 16, the display control process according to this modification example is different from the display control process (see FIG. 9) according to this embodiment in that each process in Steps S104E and S104F is performed instead of Step S104.

In Step S104E of FIG. 16, the second display control unit 84 determines whether or not the compression of the breast has been released in the mammography apparatus 10. Specifically, the second display control unit 84 according to this embodiment determines whether or not the user has input a command to release the compression of the breast in the mammography apparatus 10. In a case in which the command to release the compression has not been input, the determination result in Step S104E is "No" and the process proceeds to Step S104F.

In Step S104F, the second display control unit 84 determines whether or not a predetermined time has elapsed since the reception of the image data of the radiographic image 90 from the mammography apparatus 10. In a case in which the predetermined time has not elapsed since the reception of the image data of the radiographic image 90, that is, in a case in which the time elapsed since the reception of the image data of the radiographic image 90 is shorter than a predetermined time, the determination result in Step S104F is "No" and the process proceeds to Step S104E. On the other hand, in a case in which the predetermined time has elapsed since the reception of the image data of the radiographic image 90, a predetermined time or more has elapsed since the capture of the radiographic image 90 and this corresponds to a case in which an ultrasound image is captured. Therefore, the process proceeds to Step S106 (see FIG. 9).

In contrast, in a case in which the command to release the compression has been input, the determination result in Step S104E is "Yes" and this corresponds to a case in which an ultrasound image is not captured. Therefore, the process proceeds to Step S126 (see FIG. 9).

For example, the predetermined time in Step S104F which is used for determining whether or not to capture an ultrasound image in this modification example may be experimentally obtained in advance. Further, for example, a configuration may be used in which the user can set the predetermined time.

In this embodiment, the display and non-display of the image scale 72 can be switched by the on button 91 and the off button 92 displayed on the display unit 58. However, the configuration in which the display and non-display of the image scale 72 can be switched is not limited to this aspect.

For example, the display and non-display of the image scale 72 may be switched as follows: in a case in which the receiving unit 86 receives the position on the radiographic image 90 which has been designated by the user through the operation unit 56 and displayed on the display unit 58, the image scale 72 is displayed on the radiographic image 90; and, in a case in which the designation of the position on the radiographic image 90 has not been received, the image scale 72 is not displayed. For example, in a case in which a pointer (not illustrated) displayed on the display unit 58 is positioned on the radiographic image 90 by the operation of the user, the image scale 72 may be displayed. In a case in which the pointer is located at a position other than the radiographic image 90, the image scale 72 may not be displayed. Further, in this case, the display and non-display of the image scale 72 may be switched on the basis of whether or not a position on the breast image 90W is designated or whether or not a position on the breast image 90G is designated.

Second Embodiment

Next, a second embodiment will be described in detail.

Since the configuration of a medical imaging system 1 (see FIG. 1) and the configuration of a radiography system 2 (see FIG. 2) in this embodiment are the same as those in the first embodiment, the description thereof will not be repeated. Since an example of the functional configuration of a mammography apparatus 10 and a console 12 according to this embodiment is the same as the functional configuration of the mammography apparatus 10 and the console 12 according to Modification Example 2 of the first embodiment (see FIG. 13), the description thereof will not be repeated.

Figure 17:
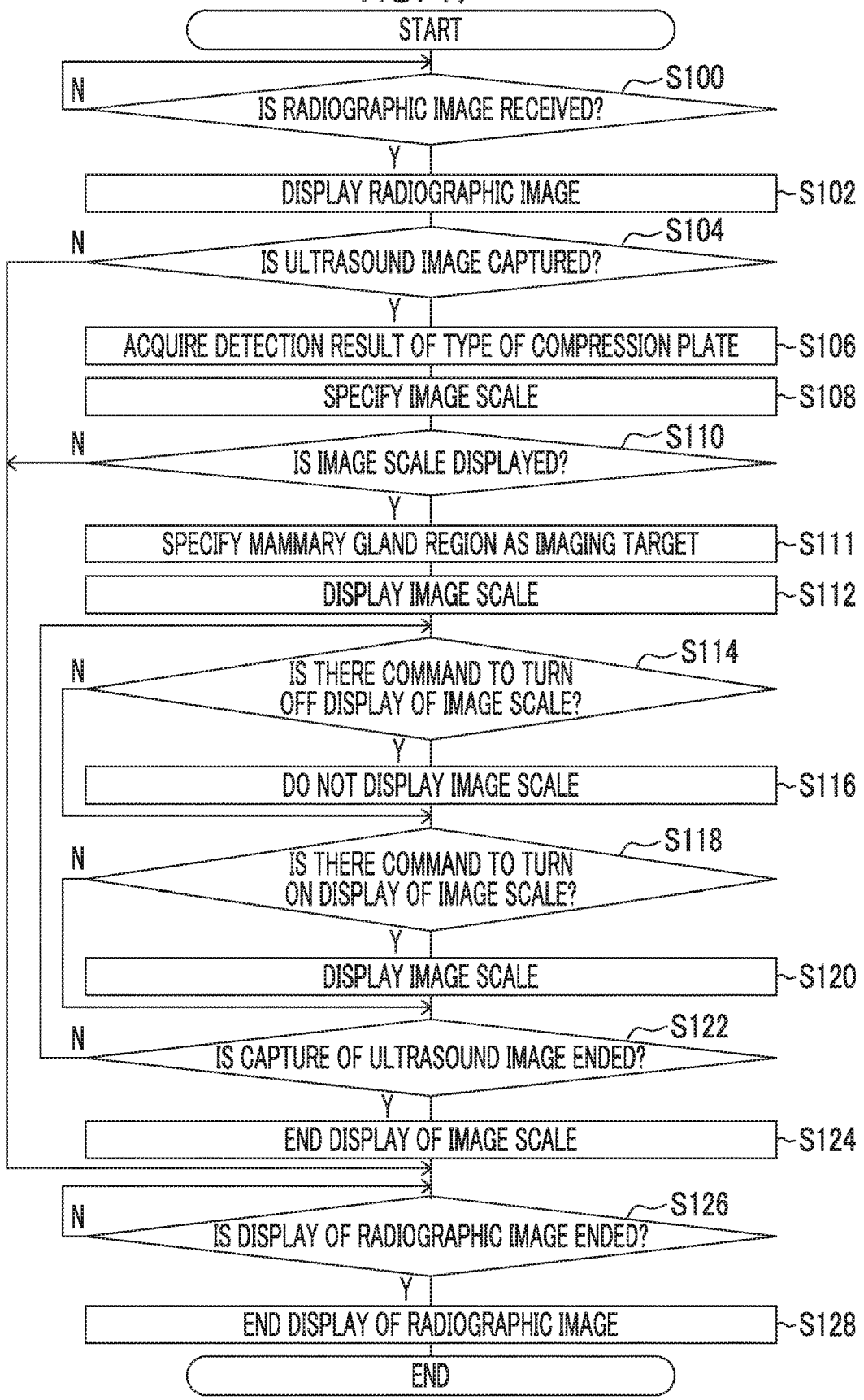
FIG. 17 is a flowchart illustrating an example of the flow of a display control process of a console according to a second embodiment.

In contrast, since a display control process according to this embodiment is partially different from the display control process according to the first embodiment (see FIG. 9), the display control process according to this embodiment will be described. FIG. 17 illustrates a portion of a flowchart illustrating an example of the flow of the position control process of the console 12 according to this embodiment. As illustrated in FIG. 17, the display control process according to this embodiment is different from the display control process according to the first embodiment (see FIG. 11) in that a process in Step S111 is performed between Steps S110 and S112.

As illustrated in FIG. 17, in this embodiment, in a case in which the determination result in Step S110 is "Yes", the process proceeds to Step S111. In Step S111, the second display control unit 84 specifies a mammary gland region whose image is to be captured from the radiographic image 90. Specifically, the second display control unit 84 specifies a region in which the size of the mammary gland region indicated by the region information is equal to or greater than a region threshold value as the mammary gland region whose image is to be captured, on the basis of the region information input from the acquisition unit 87.

Then, in Step S112, the second display control unit 84 performs control to display the image scale 72 specified in Step S108 on the radiographic image 90 displayed on the display unit 58 as described above. The second display control unit 84 according to this embodiment performs control to display the image scale 72 displayed in the form in which the position of the mammary gland region is easy to understand on the display unit 58. Hereinafter, a scale (information) indicating the position of the mammary gland image 90G in the image scale 72 is referred to as mammary gland region identification information 72G and a scale (information) indicating a position other than the mammary gland image 90G in the image scale 72 is referred as other region Information 72E.

Figure 18A:
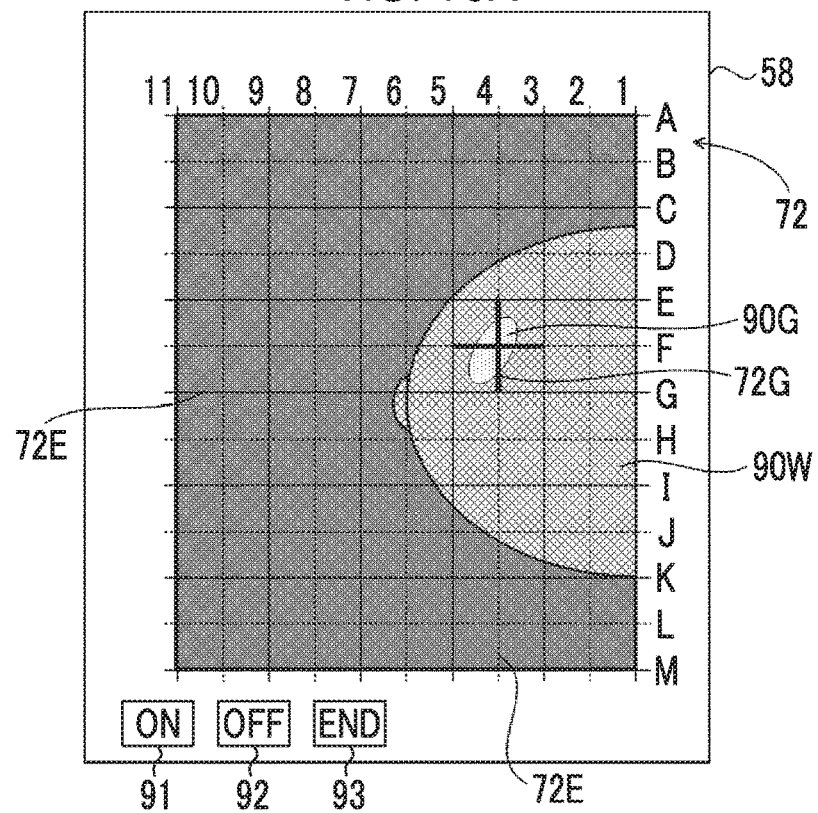
FIG. 18A is a diagram illustrating an example of an image scale displayed on a radiographic image displayed on a display unit according to the second embodiment.

FIG. 18A illustrates an example of a state in which an example of the image scale 72 according to this embodiment is displayed on the radiographic image 90. The image scale 72 illustrated in FIG. 18A includes a plurality of lines and symbols for identifying the plurality of lines, similarly to the image scale 72 according to the first embodiment (see FIG. 11). Among the plurality of lines included in the image scale 72, lines of a portion corresponding to the mammary gland image 90G are displayed in a different form from the lines of the other portions. For example, in FIG. 18A, the display forms of the mammary gland region identification information 72G and the other region identification information 72E are different from each other in that scale lines corresponding to the mammary gland region identification information 72G are thicker than scale lines corresponding to the other region identification information 72E. In FIG. 18A, as an example in which the display forms of the mammary gland region identification information 72G and the other region identification information 72E are different from each other, the thicknesses of the scale lines corresponding to these information items are different from each other. However, a method for displaying these information items in different forms is not limited to the example illustrated in FIG. 18A. For example, the mammary gland region identification information 72G and the other region identification information 72E may be displayed in different forms as follows: the scale lines corresponding to the mammary gland region identification information 72G and the other region identification information 72E are displayed in different colors; each of the scale lines is displayed so as to flicker; or each of the scale lines is displayed so as not to flicker.

Figure 18B:
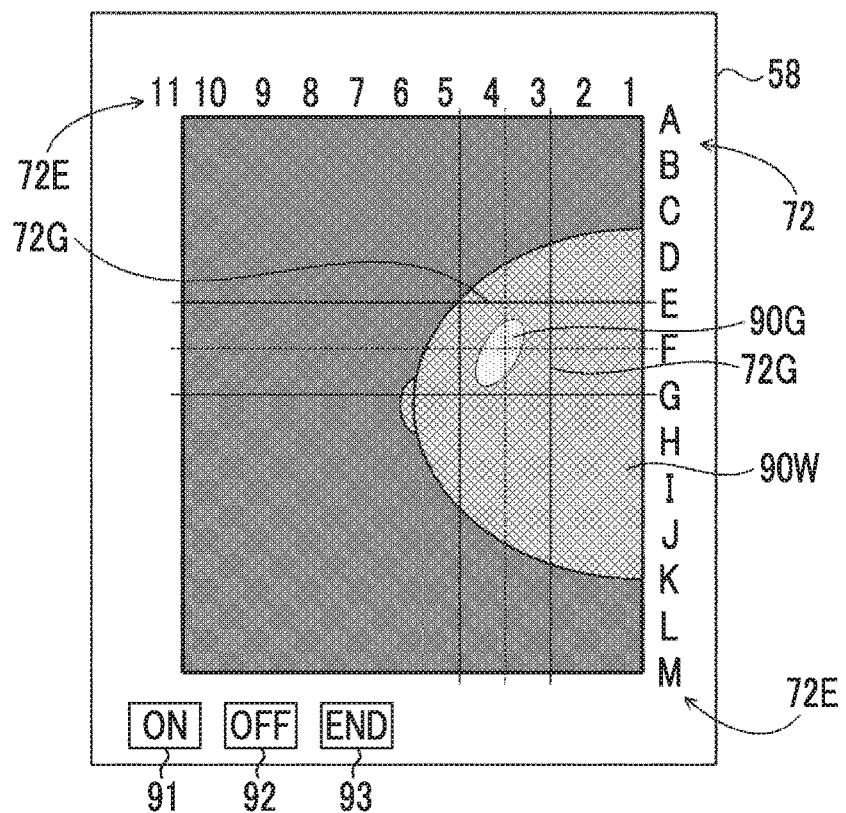
FIG. 18B is a diagram illustrating another example of the image scale displayed on the radiographic image displayed on the display unit according to the second embodiment.

For example, as in an image scale 72 illustrated in FIG. 18B, scale lines corresponding to the mammary gland image 90G may be the mammary gland region identification information 72G and symbols for identifying the scale lines may be the other region identification information 72E.

Figure 18C:
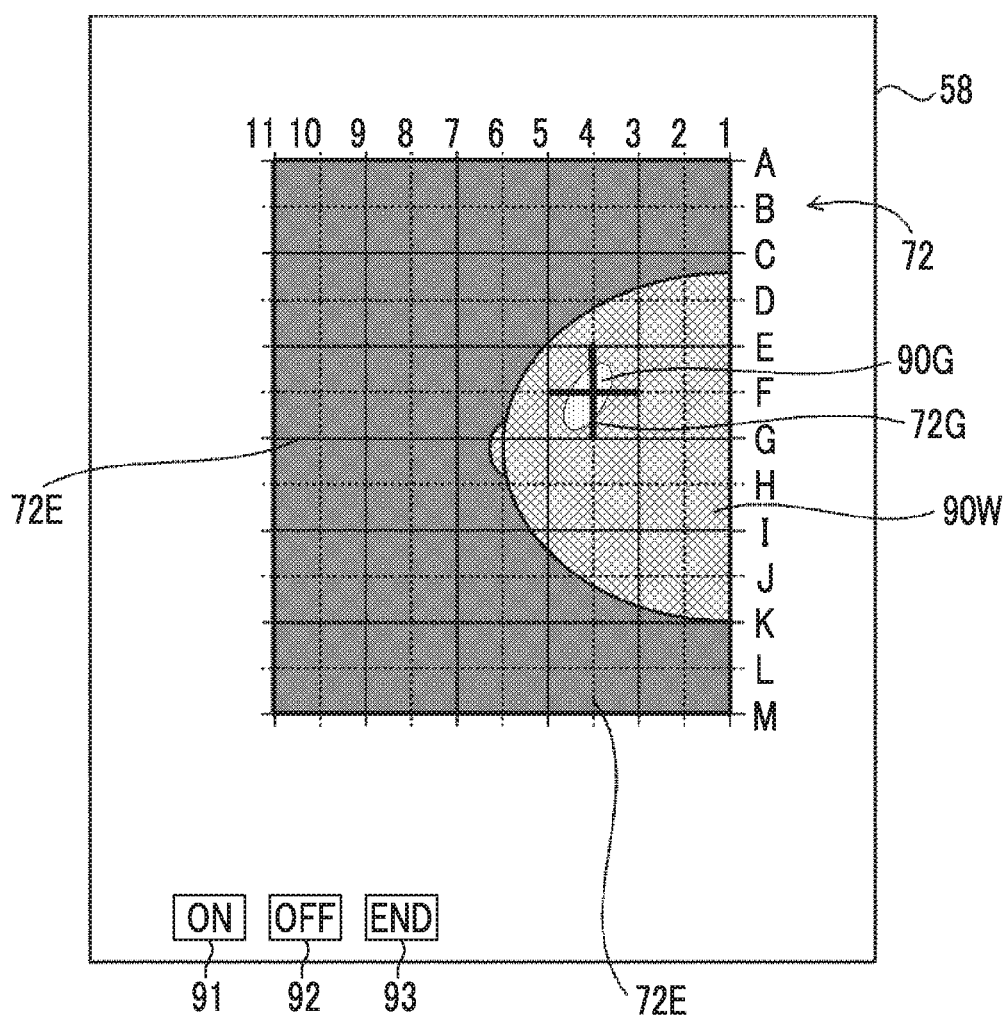
FIG. 18C is a diagram illustrating still another example of the image scale displayed on the radiographic image displayed on the display unit according to the second embodiment.

In some cases, the user operates the operation unit 56 to input a command to increase or decrease the size of the radiographic image 90 displayed on the display unit 58. In this case, the second display control unit 84 changes the image scale 72 following a change in the size of the radiographic image 90 which has been increased or decreased. FIG. 18C illustrates an example of an aspect in which a radiographic image 90 obtained by the decrease of the size of the radiographic image 90 illustrated in FIG. 18A by the first display control unit 82 is displayed on the display unit 58 in response to a command from the user. As illustrated in FIG. 18C, the second display control unit 84 displays, on the radiographic image 90, the image scale 72 in which the spacing between the scale lines has been changed following the radiographic image 90 reduced by the first display control unit 82.

Figure 19:
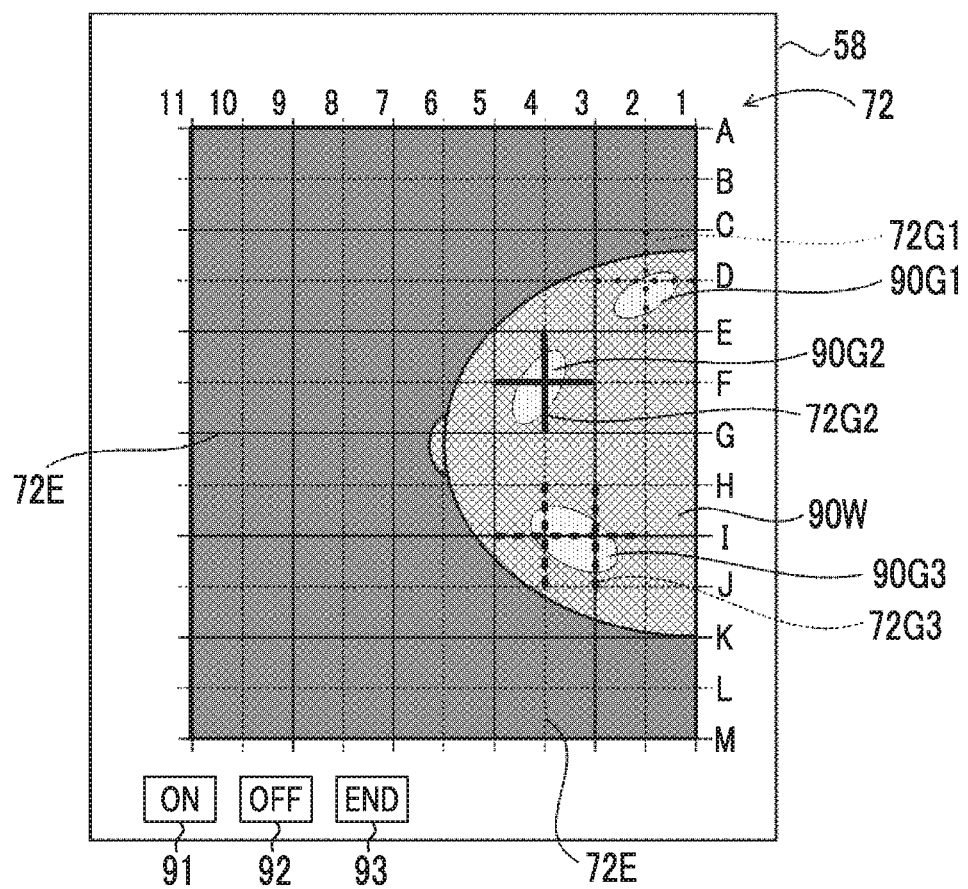
FIG. 19 is a diagram illustrating an example of an image scale displayed on a radiographic image displayed on the display unit according to the second embodiment in a case in which there are a plurality of mammary gland regions.
Figure 20:
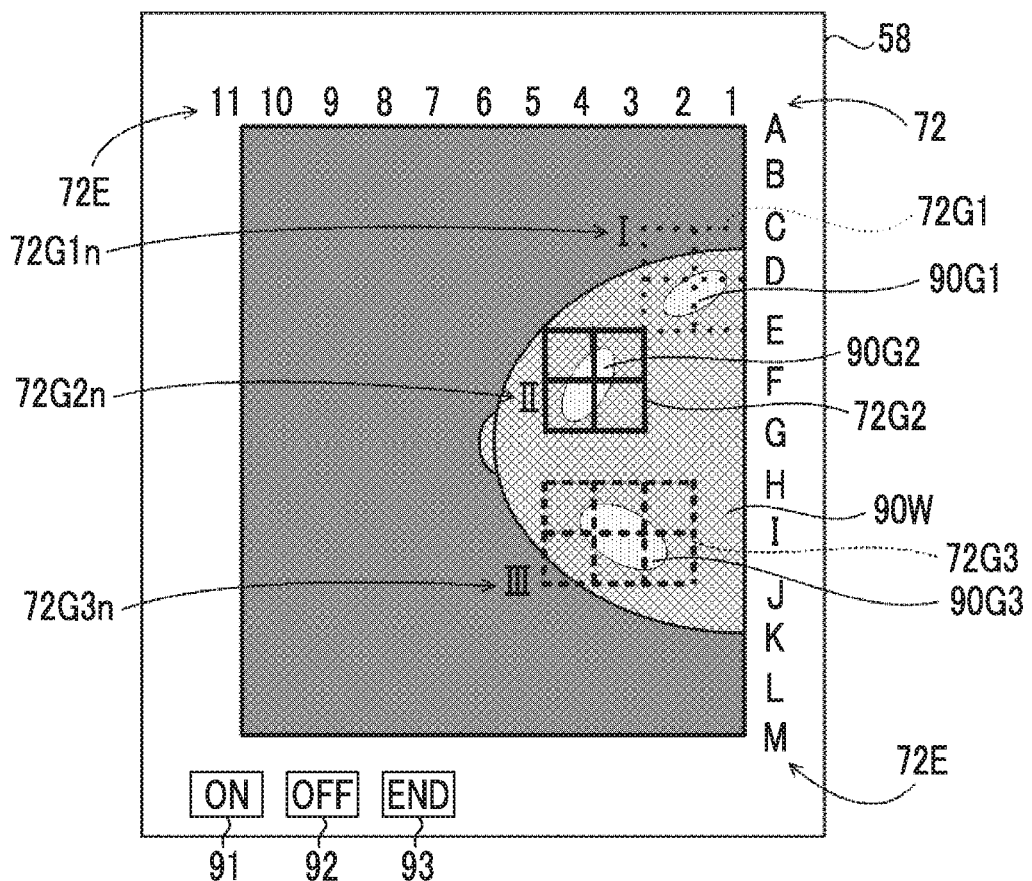
FIG. 20 is a diagram illustrating another example of the image scale displayed on the radiographic image displayed on the display unit according to the second embodiment in a case in which there are a plurality of mammary gland regions.

In a case in which there are a plurality of mammary gland regions as imaging targets specified in Step S111 of the display control process, the mammary gland region identification information items 72G for the plurality of mammary gland regions may be displayed in different forms. FIGS. 19 and 20 illustrate examples of the image scale 72 which is displayed on the radiographic image 90 displayed on the display unit 58 by the second display control unit 84 in a case in which three mammary gland regions are specified as imaging targets. The breast image 90W of the radiographic image 90 illustrated in FIGS. 19 and 20 includes mammary gland images 90G1, 90G2, and 90G3 corresponding to three mammary gland regions. In an image scale 72 illustrated in FIG. 19 and FIG. 20, a scale line which is mammary gland region identification information 72G1 corresponding to the mammary gland image 90G1, a scale line which is mammary gland region identification information 72G2 corresponding to the mammary gland image 90G2, and a scale line which is mammary gland region identification information 72G3 corresponding to the mammary gland image 90G3 are different types.

As in an image scale 72 illustrated in FIG. 20, identifiers 72G1*n* to 72G3*n* for identifying the mammary gland images 90G1 to 90G3, respectively, may be given. Specifically, "I" which is the identifier 72G1*n* corresponds to the mammary gland image 90G1, "II" which is the identifier 72G2*n* corresponds to the mammary gland image 90G2, and "III" which is the identifier 72G3*n* corresponds to the mammary gland image 90G3. Numbers (Roman numerals in FIG. 20) represented by these identifiers may indicate the order in which ultrasound images are captured. In a case in which the identifiers 72G1n to 72G3n are identifiers indicating order, such as numbers, the identifiers may be assigned in any order, such as the order in which the mammary gland regions are specified as imaging targets by the second display control unit 84 or may be assigned in the order which is specified by the user through the operation unit 56.

Figure 21A:
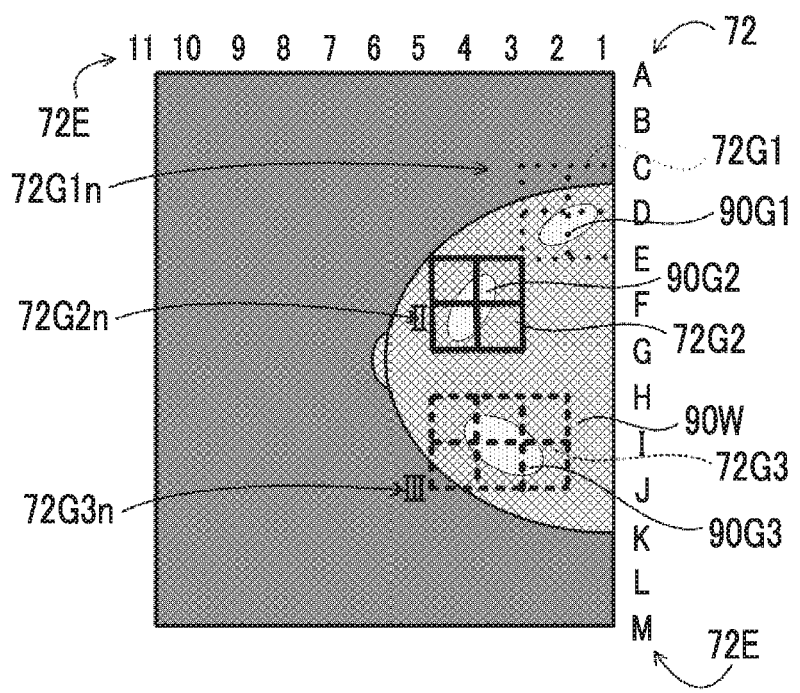
FIG. 21A is a diagram illustrating an example in which corresponding mammary gland region identification information items are displayed in different forms in a mammary gland image of a mammary gland region for which the capture of an ultrasound image has ended and a mammary gland image of a mammary gland region for which the capture of an ultrasound image has not ended.
Figure 21B:
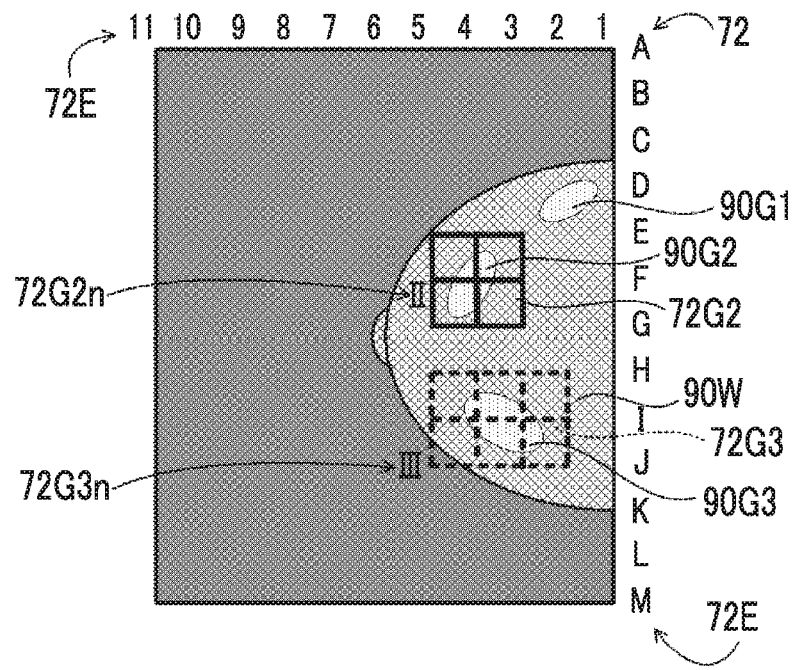
FIG. 21B is a diagram illustrating an example in which the corresponding mammary gland region identification information items are displayed in different forms in the mammary gland image of the mammary gland region for which the capture of an ultrasound image has ended and the mammary gland image of the mammary gland region for which the capture of an ultrasound image has not ended.
Figure 21C:
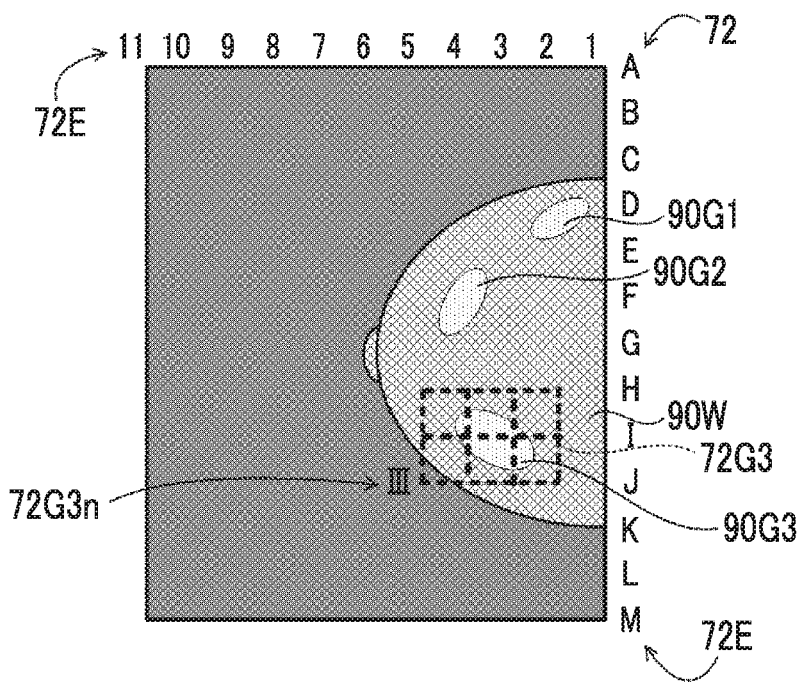
FIG. 21C is a diagram illustrating an example in which the corresponding mammary gland region identification information items are displayed in different forms in the mammary gland image of the mammary gland region for which the capture of an ultrasound image has ended and the mammary gland image of the mammary gland region for which the capture of an ultrasound image has not ended.
Figure 21D:
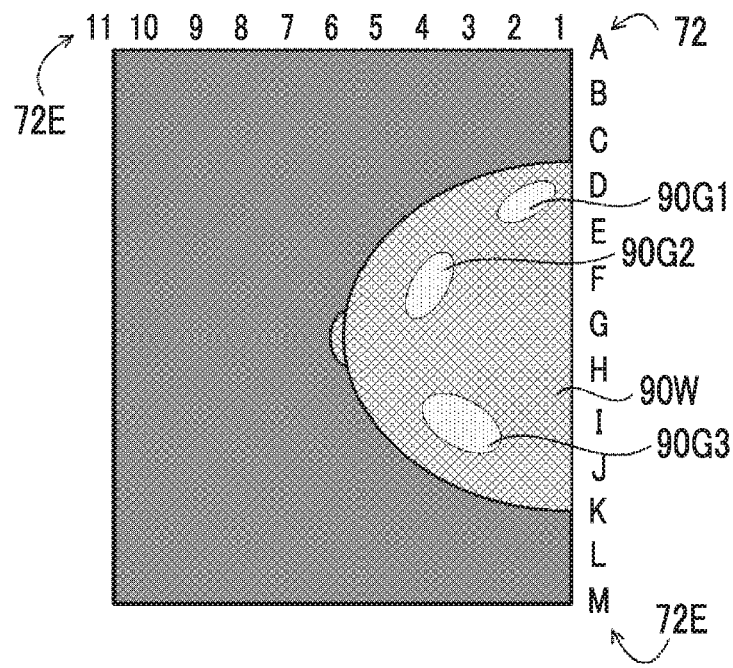
FIG. 21D is a diagram illustrating an example in which the corresponding mammary gland region identification information items are displayed in different forms in the mammary gland image of the mammary gland region for which the capture of an ultrasound image has ended and the mammary gland image of the mammary gland region for which the capture of an ultrasound image has not ended.

As illustrated in FIGS. 19 and 20, in a case in which a plurality of mammary gland images 90G (90G1 to 90G3) are included in the radiographic image 90 and ultrasound images are sequentially captured for each of the mammary gland images 90G, the mammary gland region identification information items 72G corresponding to the mammary gland image 90G for which the capture of an ultrasound image has ended and the mammary gland image 90G for which the capture of an ultrasound image has not ended may be displayed in different forms. A case in which this embodiment is applied to the image scale 72 illustrated in FIG. 20 will be described with reference to FIGS. 21A to 21D. In this embodiment, it is assumed that the user sequentially takes ultrasound images for the mammary gland image 90G1, the mammary gland image 90G2, and the mammary gland image 90G3 in this order. Until the capture of an ultrasound image of the mammary gland region corresponding to the mammary gland image 90G1 ends, the image scale 72 displayed on the display unit 58 includes the mammary gland region identification information items 72G1, 72G2, and 72G3 as illustrated in FIG. 21A. In a case in which the capture of the ultrasound image of the mammary gland region corresponding to the mammary gland image 90G1 ends, the second display control unit 84 does not display the mammary gland region identification information 72G1 and the identifier 72G1n as illustrated in FIG. 21B. Further, in a case in which the capture of the ultrasound image of the mammary gland region corresponding to the mammary gland image 90G2 ends, the second display control unit 84 does not display the mammary gland region identification information 72G2 and the identifier 72G2n as illustrated in FIG. 21C. Furthermore, in a case in which the capture of the ultrasound image of the mammary gland region corresponding to the mammary gland image 90G3 ends, the second display control unit 84 does not display the mammary gland region identification information 72G3 and the identifier 72G3n as illustrated in FIG. 21D.

As described above, in a case in which there are a plurality of mammary gland regions as imaging targets, the mammary gland region identification information items 72G corresponding to the mammary gland image 90G for which the capture of an ultrasound image has ended and the mammary gland image 90G for which the capture of an ultrasound image has not ended are displayed in different forms. Therefore, it is easy for the user to determine whether or not imaging has been completed.

In the examples illustrated in FIGS. 21A to 21D, the aspect in which the mammary gland region identification information 72G corresponding to the mammary gland image 90G of the mammary gland region for which the capture of an ultrasound image has ended is not displayed to make a difference in display form has been described. However, a method for making the display forms different from each other is not limited to this embodiment.

The method by which the second display control unit 84 recognizes whether or not the capture of the image of each mammary gland region has ended is not particularly limited. The following configuration may be used: the user inputs information indicating that imaging has ended through the display unit 58 of the console 12 or the operation unit 66 of the ultrasonography apparatus 16; and, in a case in which the information from the user is received, the second display control unit 84 recognizes that imaging has ended. Further, for example, the mammography apparatus 10 may comprise an imaging device. In a case in which the imaging device captures an image of an aspect in which the user takes an ultrasound image, the second display control unit 84 may analyze the image captured by the imaging device and recognize the capture of the ultrasound image on the basis of the analysis result.

As described above, according to this embodiment, since the mammary gland region identification information 72G and the other region identification information 72E are displayed in different forms, it is easy to determine the position of the mammary gland image 90G.

Figure 22:
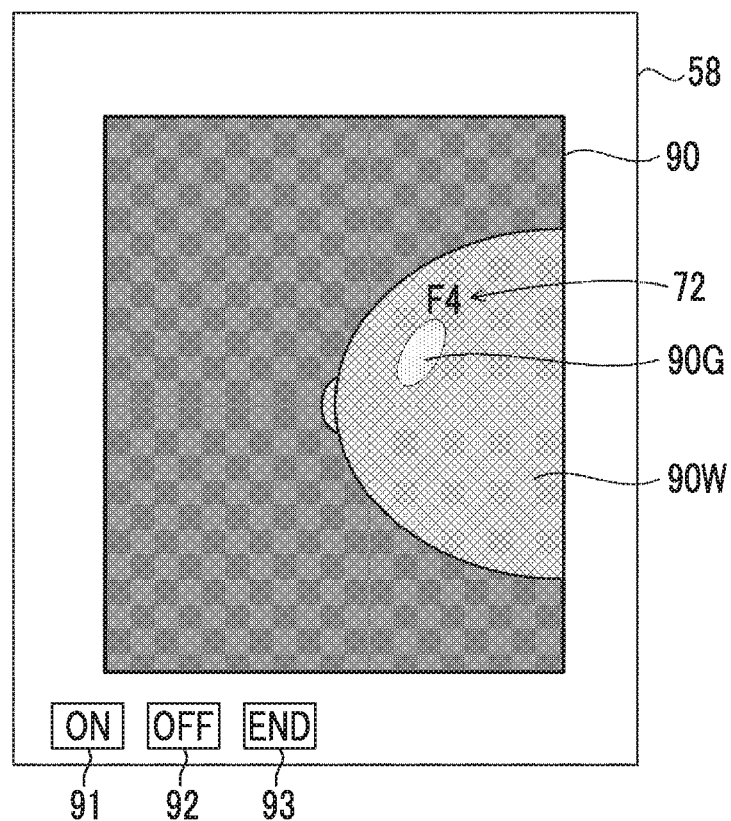
FIG. 22 is a diagram illustrating another example of the image scale displayed on the radiographic image displayed on the display unit according to the second embodiment.

The image scale 72 in which the position of the mammary gland region is displayed in an easy-to-understand manner is not limited to the aspect in which the image scale 72 includes the other region identification information 72E and the mammary gland region identification information 72G as illustrated in FIGS. 18A to 21D. For example, the image scale 72 may be configured to include only information indicating the position of the mammary gland region, specifically, the position of the mammary gland image 90G on the radiographic image 90. FIG. 22 illustrates an example of a state in which an example of the image scale 72 including only information indicating the position of the mammary gland image 90G is displayed on the radiographic image 90. FIG. 22 illustrates a state in which "F4" which is information for identifying the position of the mammary gland image 90G is displayed as the image scale 72 in the vicinity of the mammary gland image 90G. In the example illustrated in FIG. 22, the image scale 72 displayed as "F4" enables the user to recognize that the position of "F4" on the compression plate scale 70 of the compression plate 34 corresponds to the mammary gland region.

In a case in which the display unit 58 includes a device that outputs sound, such as a speaker, the position of the mammary gland image 90G may be audibly displayed by sound. For example, in a case in which it is difficult for the user to see the display unit 58 of the console 12 at the position where the user takes an ultrasound image, it is preferable that the position of the mammary gland image 90G is audibly displayed. In this case, the user does not need to check the position of the mammary gland image 90G with the display unit 58 and it is easy for the user to take an ultrasound image.

Further, in this embodiment, the second display control unit 84 of the console 12 specifies the mammary gland region. However, a method for specifying the mammary gland region is not limited to this embodiment. For example, the following configuration may be used: the user operates the operation unit 56 to designate the position of the mammary gland image 90G on the radiographic image 90; the acquisition unit 87 acquires the position specified by the user; and the mammary gland region is determined on the basis of the designated position.

Third Embodiment

Next, a third embodiment will be described in detail.

Figure 23:
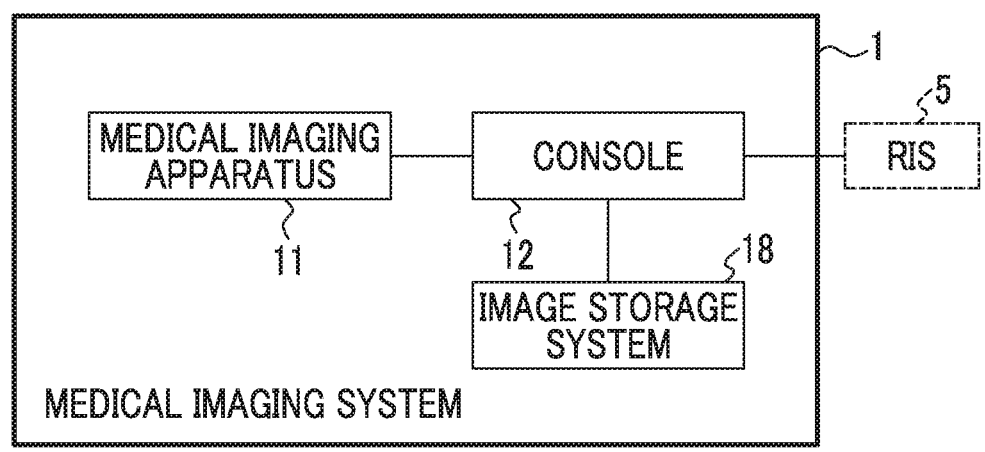
FIG. 23 is a diagram schematically illustrating an example of the overall configuration of a medical imaging system according to a third embodiment.

FIG. 23 is a diagram illustrating an example of the overall configuration of a medical imaging system 1 according to this embodiment. As illustrated in FIG. 23, the medical imaging system 1 according to this embodiment differs from the medical imaging system 1 (see FIG. 1) according to the first embodiment in that it comprises a medical imaging apparatus 11 instead of the mammography apparatus 10 and the ultrasonography apparatus 16.

The medical imaging apparatus 11 is an apparatus that is configured by combining the mammography apparatus 10 and the ultrasonography apparatus 16 according to the first embodiment, that is, an apparatus that can capture a radiographic image and an ultrasound image of the breast. For example, the medical imaging apparatus 11 according to this embodiment is a mammography apparatus that can capture an ultrasound image. The medical imaging apparatus 11 according to this embodiment corresponds to an example of a mammography apparatus according to the present disclosure.

Figure 24:
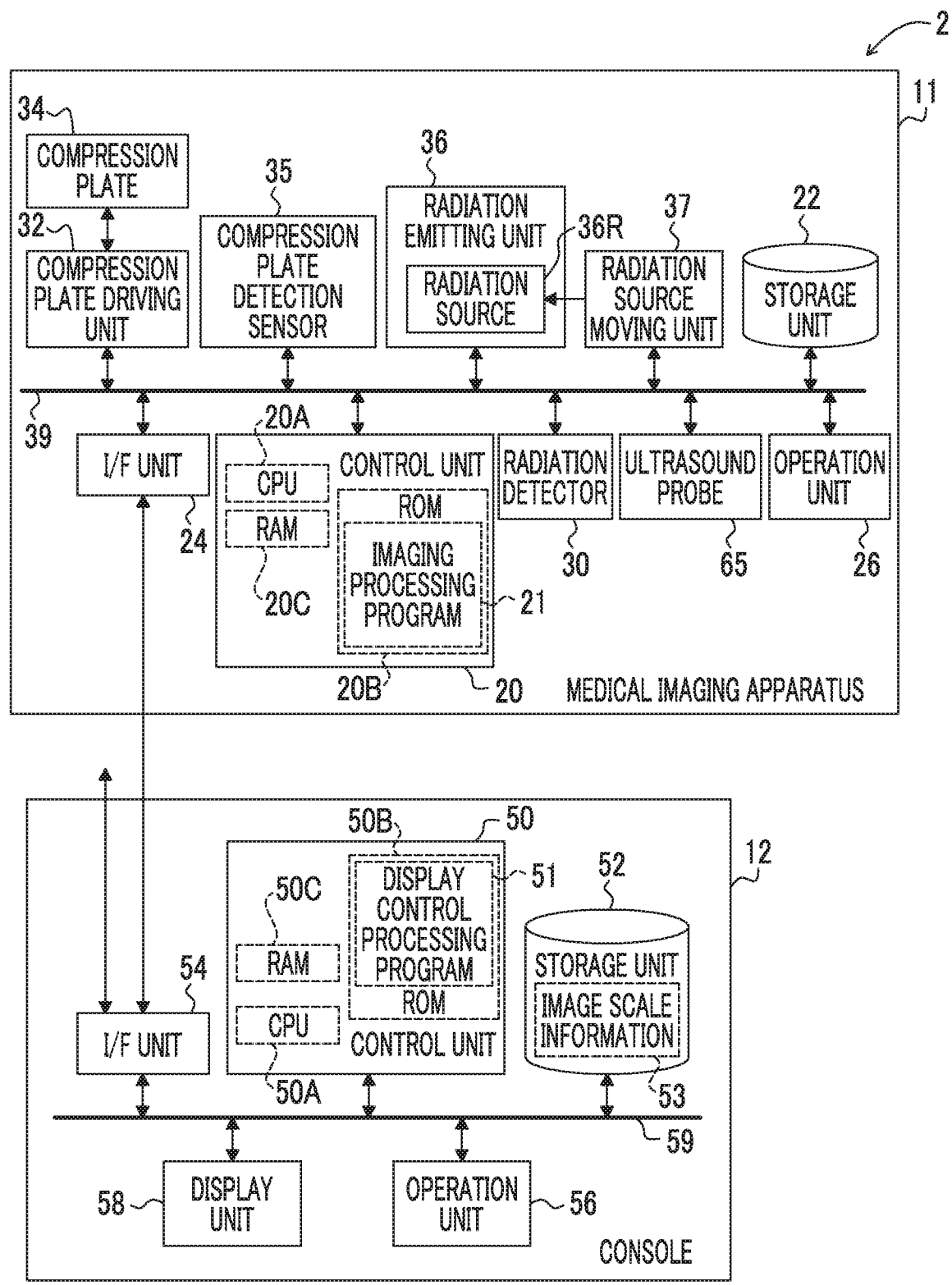
FIG. 24 is a block diagram illustrating an example of the configuration of a console and a medical imaging apparatus according to the third embodiment.

FIG. 24 is a block diagram illustrating an example of the configuration of the medical imaging apparatus 11 and the console 12 according to this embodiment. As illustrated in FIG. 24, the medical imaging apparatus 11 according to this embodiment differs from the mammography apparatus 10 according to the first embodiment in that it further comprises an ultrasound probe 65. The ultrasound probe 65 included in the medical imaging apparatus 11 is a so-called handheld type, like the ultrasound probe 65 according to each of the above-described embodiments. The user can operate the ultrasound probe 65 to capture an ultrasound image. For example, in the medical imaging apparatus 11 according to this embodiment, the ultrasound probe 65 is attachably and detachably provided in the mammography apparatus 10. For example, the ultrasound probe 65 is attachable to and detachable from the arm portion 42.

Since the functional configuration of the medical imaging apparatus 11 is the same as the functional configuration of the mammography apparatus 10 according to the first embodiment (see FIG. 6), the description thereof will not be repeated. In addition, since a display control process performed by the console 12 according to this embodiment is the same as the display control process (see FIG. 9) performed by the console 12 according to the first embodiment, the description thereof will not be repeated.

As described above, the ultrasound probe 65 included in the medical imaging apparatus 11 according to this embodiment is a so-called handheld type. Therefore, in a case in which an ultrasound image is captured after capturing a radiographic image in continuous capturing, the user takes an ultrasound image with reference to the radiographic image 90 captured first as in the radiography system 2 according to each of the above-described embodiments.

Therefore, in the medical imaging apparatus 11 according to this embodiment, the console 12 performs the display control process such that the correspondence between a position on the radiographic image 90 and a position on the compression plate 34 is easily understood as in the first embodiment. Therefore, it is possible for the user to easily take an ultrasound image.

Further, in this embodiment, since the medical imaging apparatus 11 has a function of capturing an ultrasound image, the overall size of the apparatus can be less than that in a case in which the mammography apparatus 10 and the ultrasonography apparatus 16 are separately provided.

As described above, the radiography system 2 according to each of the above-described embodiments includes the mammography apparatus 10 or the medical imaging apparatus 11 and the console 12. The compression plate 34 provided in the mammography apparatus 10 or the medical imaging apparatus 11 compresses the breast disposed between the radiation source 36R and the radiation detector 30. In addition, in the compression plate 34, the compression plate scale 70 for identifying the in-plane position of the upper surface 34A which is irradiated with the radiation R from the radiation source 36R, the lower surface 34D which is opposite to the upper surface 34A and comes into contact with the breast, or a surface that is parallel to the upper surface 34A between the upper surface 34A and the lower surface 34D is given to any one of the upper surface 34A, the lower surface 34D, or the parallel surface. The console 12 comprises the first display control unit 82 and the second display control unit 84. The first display control unit 82 performs control to display the radiographic image 90 captured by the mammography apparatus 10 or the medical imaging apparatus 11 on the display unit 58. The second display control unit 84 performs control to display the image scale 72 indicating a position on the radiographic image 90 which corresponds to the in-plane position of the compression plate 34 on the radiographic image 90 displayed on the display unit 58.

In some cases, the compression plate scale 70 provided on the compression plate 34 varies depending on the type of the compression plate 34. However, according to the radiography system 2 of each of the above-described embodiments, the second display control unit 84 can display an appropriate image scale 72 which corresponds to the compression plate scale 70 provided in the compression plate 34 on the radiographic image 90.

Therefore, in the radiography system 2 according to the above-described embodiments, the above-mentioned configuration makes it possible for the user to easily understand the correspondence between a position on the radiographic image 90 and a position on the compression plate 34 in a case in which an ultrasound image is captured with reference to the radiographic image 90 captured first in continuous imaging.

Since the correspondence between the position on the radiographic image 90 and the position on the compression plate 34 can be easily understood, for example, the user can easily check the position of the mammary gland region on the compression plate 34 and can easily take an ultrasound image. In addition, the user can easily take the image of an appropriate region. In addition, in a case in which it is difficult to capture an ultrasound image, the time required for capturing an ultrasound image increases and the time for which the breast of the subject is continuously compressed increases. Therefore, the burden on the subject is likely to increase. According to the radiography system 2 of each of the above-described embodiments, it is possible to suppress an increase in the time required for capturing an ultrasound image and thus to suppress an increase in the burden on the subject.

Further, the compression plate scale 70 which is provided on the compression plate 34 attached to the mammography apparatus 10 according to each of the above-described embodiments is not included in the radiographic image 90. Therefore, unlike the case in which positioning scales and markers provided on the compression plate 34 are included in the radiographic image 90, the above-mentioned configuration enables the user to easily interpret the radiographic image 90 without hindering the user who interprets the radiographic image 90.

In addition, in the radiography system 2 according to each of the above-described embodiments, the image scale 72 is displayed on the radiographic image 90 in a case in which an ultrasound image is captured. The image scale 72 is not displayed on the radiographic image 90 in a case in which an ultrasound image is not captured. Further, in the radiography system 2 according to each of the above-described embodiments, the display and non-display of the image scale 72 on the radiographic image 90 can be switched. Therefore, it is possible to prevent the image scale 72 from hindering the user who interprets the radiographic image 90.

Figure 25A:
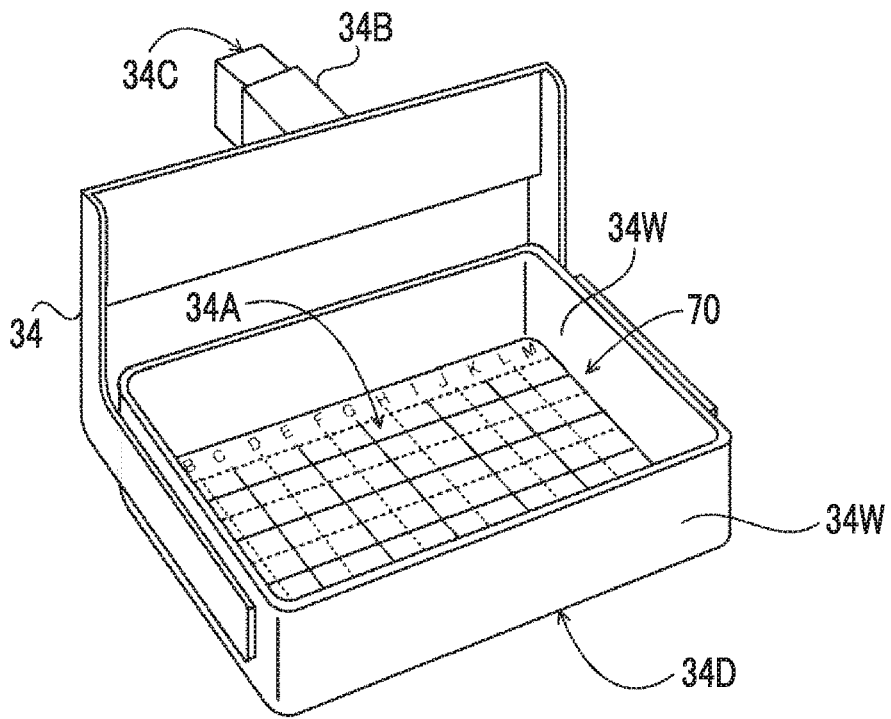
FIG. 25A is a perspective view illustrating another example of the compression plate.
Figure 25B:
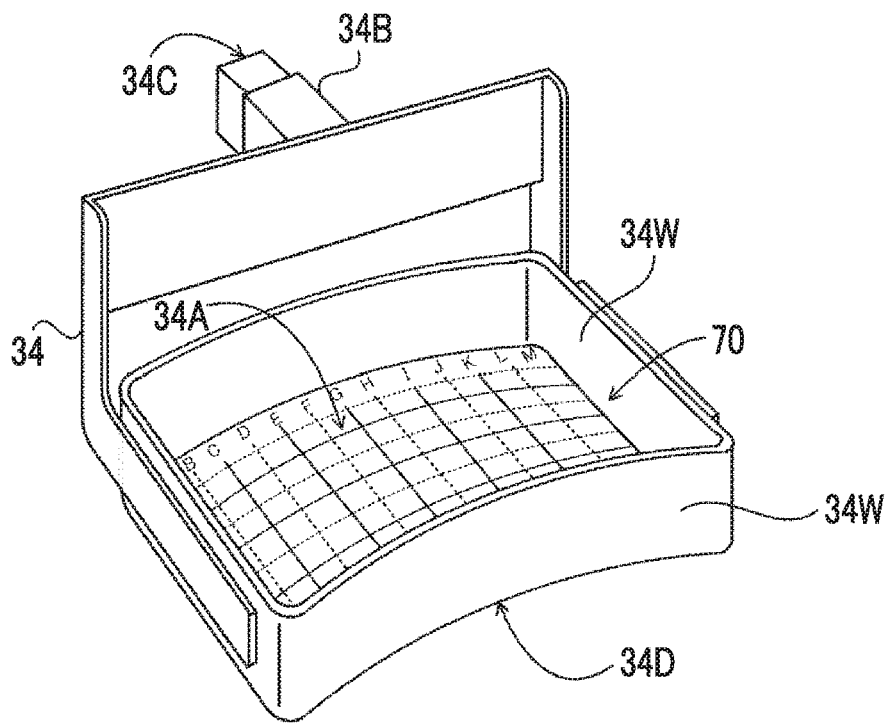
FIG. 25B is a perspective view illustrating still another example of the compression plate.

The compression plate 34 provided in the mammography apparatus 10 or the medical imaging apparatus 11 is not limited to the form of the compression plate 34 illustrated in each of the above-described embodiments. For example, as in a compression plate 34 illustrated in FIG. 25A, a wall surface 34W that extends toward the radiation source 36R may be provided around the upper surface 34A. In addition, for example, as illustrated in FIG. 25B, a compression plate 34 may be curved according to the shape of the breast. At least the lower surface 34D which comes into contact with the breast may be curved in a convex shape toward the radiation source 36R according to the shape of the breast.

Further, for example, the compression plate 34 may be inclined or deformed in the direction from the chest wall to the nipple or may be inclined or deformed in the left-right direction of the subject, according to the hardness and shape of the breast.

Figure 25C:
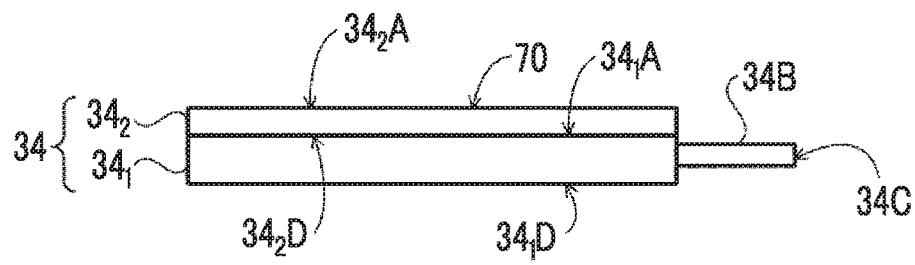
FIG. 25C is a side view illustrating yet another example of the compression plate.
Figure 25D:
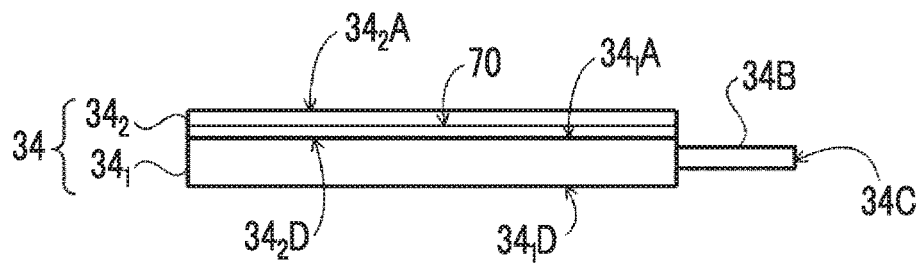
FIG. 25D is a side view illustrating still yet another example of the compression plate.

Furthermore, for example, as illustrated in FIG. 25C, the compression plate 34 may include a plurality of compression members. In the compression plate 34 illustrated in FIG. 25C, a compression member $34_2$ having an upper surface $34_2$A on which the compression plate scale 70 is given is provided on an upper surface $34_1$A of a compression member $34_1$. The compression member $34_2$ is attachable to and detachable from the compression member $34_1$. The compression member $34_1$ of the compression plate 34 illustrated in FIG. 25C is an example of a first compression member according to the present disclosure and the compression member $34_2$ is an example of a second compression member according to the present disclosure. As such, in a case in which the compression plate 34 includes a plurality of compression members, the position where the compression plate scale 70 is provided is not limited to the position on the compression plate 34 illustrated in FIG. 25C. For example, the compression plate scale 70 may be provided on any one of the upper surface $34_1$A and the lower surface $34_1$D of the compression member $34_1$ and the upper surface $34_2$A and the lower surface $34_2$D of the compression member $34_2$. Further, for example, the compression plate scale 70 may be provided on a surface which is parallel to the upper surface $34_1$A between the upper surface $34_1$A and the lower surface $34_1$D of the compression member $34_1$ and a surface which is parallel to the upper surface $34_2$A between the upper surface $34_2$A and the lower surface $34_2$D of the compression member $34_2$. For example, FIG. 25D illustrates a side view of an example of the compression plate 34 in which the compression plate scale 70 is provided on the plane parallel to the upper surface $34_2$A between the upper surface $34_2$A and the lower surface $34_2$D of the compression member $34_2$. The compression plate 34 illustrated in FIG. 25D is an example of a compression plate in which the compression plate scale 70 is provided on a third surface according to the present disclosure and the surface on which the compression plate scale 70 is provided is an example of the third surface according to the disclosure. Examples of a method for providing the compression plate scale 70 in the compression plate 34 in this way include a method for engraving the compression plate scale 70 in the compression plate 34 using laser processing and a method for placing the compression plate scale 70 inside the compression plate 34.

Figure 26A:
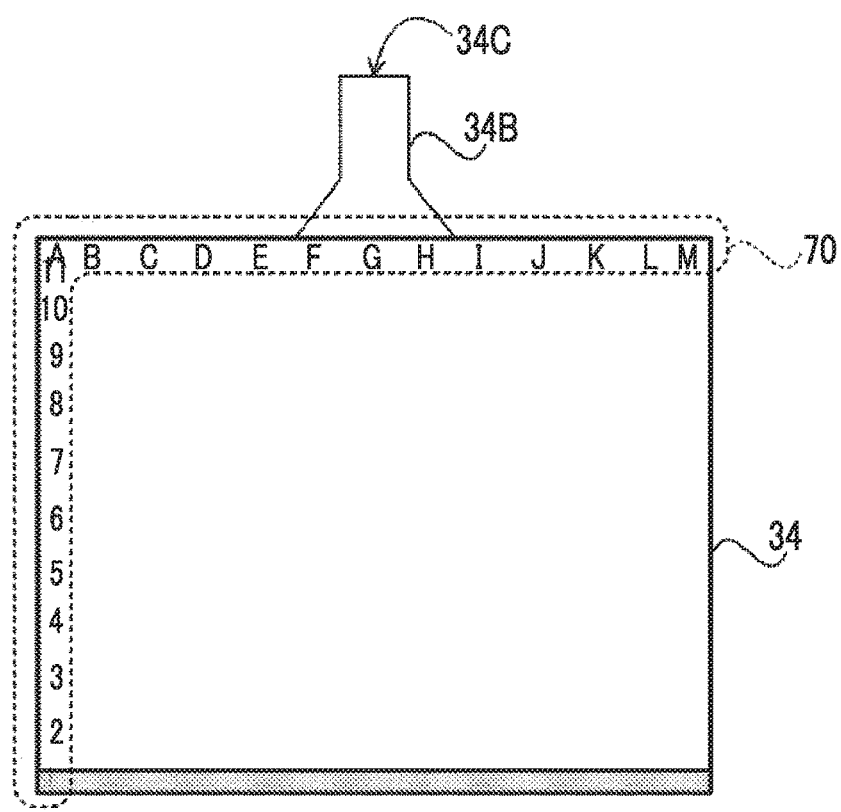
FIG. 26A is a diagram illustrating another example of the compression plate scale.
Figure 26B:
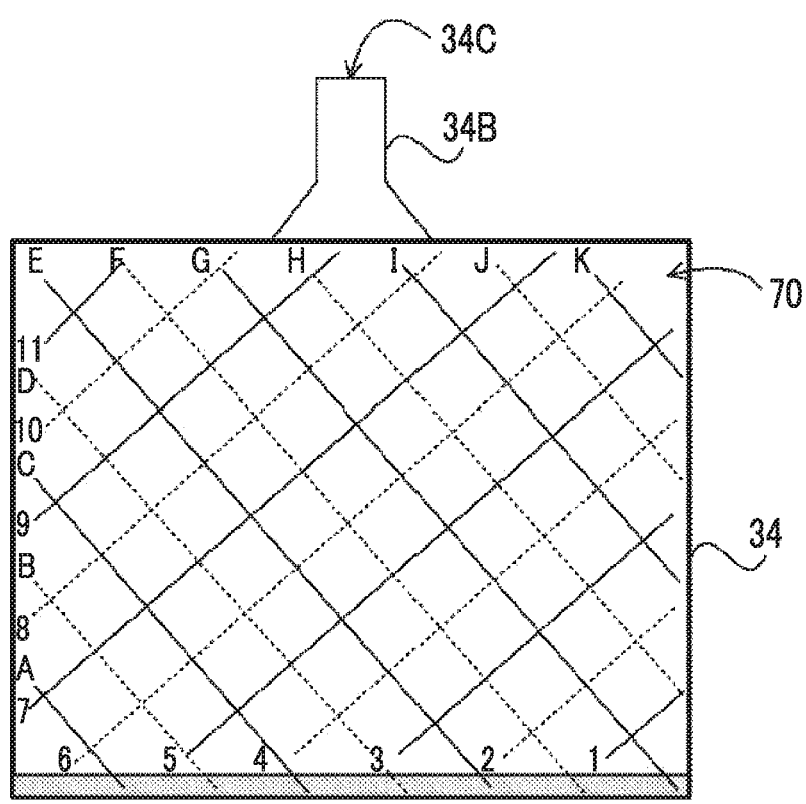
FIG. 26B is a diagram illustrating still another example of the compression plate scale.

In addition, the compression plate scale 70 and the image scale 72 are not limited to the forms of the compression plate scale 70 and the image scale 72 illustrated in each of the above-described embodiments, respectively. For example, as illustrated in FIG. 26A, a compression plate scale 70 may include only symbols indicating scales (positions). Further, for example, as in a compression plate scale 70 illustrated in FIG. 26B, lines indicating the scales may be inclined or may have a grid shape. As such, the forms of the compression plate scale 70 and the image scale 72 are not limited as long as they have information capable of identifying a position on the compression plate 34 and a position on the radiographic image 90 and may not be scales. In addition, as long as the correspondence relationship between the position on the upper surface 34A of the compression plate 34 and the position on the radiographic image 90 can be identified, the form of the compression plate scale 70 and the form of the image scale 72 do not have to be the same. For example, the compression plate scale 70 may have the form illustrated in FIG. 26A and the image scale 72 may have the form illustrated in FIG. 11.

In each of the above-described embodiments, the aspect in which the console 12 functions as the first display control unit 82 and the second display control unit 84 according to the present disclosure has been described. However, the apparatus that functions as the first display control unit 82 and the second display control unit 84 is not limited to each of the above-described embodiments. For example, another apparatus, such as the ultrasonography apparatus 16, in the medical imaging system 1 may function as at least one of the first display control unit 82 or the second display control unit 84. Further, the apparatus that functions as the first display control unit 82 and the apparatus that functions as the second display control unit 84 may be different from each other. Furthermore, in each of the above-described embodiments, the aspect in which the radiographic image 90 is displayed on the display unit 58 of the console 12 has been described. However, the display device on which the radiographic image 90 is displayed not limited to the display unit 58. For example, in a case in which the display unit 68 of the ultrasonography apparatus 16 or the medical imaging system 1 comprises a mobile terminal apparatus, the radiographic image 90 may be displayed on the mobile terminal apparatus comprised in the medical imaging system 1.

In each of the above-described embodiments, for example, the following various processors can be used as the hardware structure of processing units performing various processes such as the detection unit 80, the first display control unit 82, the second display control unit 84, and the receiving unit 86. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the display control processing program 51 is stored (installed) in the ROM 50B in advance has been described. However, the invention is not limited thereto. The display control processing program 51 may be recorded on a recording medium, such as a compact disc read only memory (CD-ROM), a digital versatile disc read only memory (DVD-ROM), or a universal serial bus (USB) memory, and then provided. In addition, the display control processing program 51 may be downloaded from an external apparatus through the network.

For example, the configurations and operations of the medical imaging system 1, the radiography system 2, and the mammography apparatus 10 described in each of the above-described embodiments are illustrative and may be changed according to the situation, without departing from the scope and spirit of the invention. In addition, the above-described embodiments may be appropriately combined with each other.

What is claimed is:

1. A radiography system comprising:
a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures a radiographic image of the breast in the compressed state using the radiation detector;
a first display processor that performs control to display the radiographic image captured by the mammography apparatus on a display device; and
a second display processor that performs control to display second position identification information which indicates a position on the radiographic image corresponding to the in-plane position of the compression member and corresponds to the first position identification information on the radiographic image displayed on the display device,
wherein the second display processor performs control to display the second position identification information during continuous imaging, and the continuous imaging captures an ultrasound image of the breast while maintaining the compressed state after capturing the radiographic image and scanning the first surface of the compression member by using an ultrasonography apparatus, and
wherein, in a case in which the continuous imaging is performed and the radiographic image includes a plurality of mammary gland regions, the second display processor displays the second position identification information in different forms in a mammary gland region for which the capture of the ultrasound image has ended and a mammary gland region for which the capture of the ultrasound image has not ended.

2. The radiography system according to claim 1, wherein the second display processor performs control to display the second position identification information in a case in which the compression member maintains the compressed state for a predetermined time or more after the radiographic image is captured.

3. The radiography system according to claim 1, wherein the second display processor acquires mammary gland amount information indicating an amount of mammary gland in the breast, and
wherein the second display processor performs the continuous imaging in a case in which the amount of mammary gland indicated by the mammary gland amount information is equal to or greater than a predetermined amount of mammary gland.

4. The radiography system according to claim 1, wherein the second display processor acquires region information indicating a mammary gland region in the breast on the basis of the radiographic image, and
wherein the second display processor performs the continuous imaging in a case in which a size of the mammary gland region indicated by the region information is equal to or greater than a predetermined size.

5. The radiography system according to claim 1, wherein the second display processor ends the display of the second position identification information in a case in which the capture of the ultrasound image has ended.

6. The radiography system according to claim 1, wherein the second display processor ends the display of the second position identification information in a case in which the compression of the breast by the compression member is released after the second position identification information is displayed.

7. The radiography system according to claim 1, wherein the radiographic image does not include an image of the first position identification information.

8. The radiography system according to claim 1, wherein the second display processor detects a type of the compression member,
wherein the first position identification information is predetermined according to the type of the compression member, and
wherein the second display processor performs control to display the second position identification information corresponding to the detected type of the compression member.

9. The radiography system according to claim 1, wherein, in a case in which the mammography apparatus includes a compression member to which the first position identification information is not given, instead of the compression member to which the first position identification information is given, and captures the radiographic image of the breast compressed by the compression member to which the first position identification information is not given, the second display processor performs control not to display the second position identification information.

10. The radiography system according to claim 1, wherein the second display processor performs control to display the second position identification information in the mammary gland region of the breast included in the radiographic image.

11. The radiography system according to claim 1, wherein the second display processor receives designation of a position on the radiographic image displayed on the display device, and
  wherein the second display processor performs control to display the second position identification information in a case in which the second display processor receives the designation of the position on the radiographic image.

12. The radiography system according to claim 1, wherein the second display processor receives designation of a position on the radiographic image displayed on the display device, and
  wherein the second display processor performs control to display the second position identification information in a case in which the position on the radiographic image received by the second display processor is a position in the mammary gland region of the breast.

13. The radiography system according to claim 1, wherein the second display processor performs control to display the second position identification information for the mammary gland region of the breast in the radiographic image and the second position identification information for a region other than the mammary gland region in different forms.

14. The radiography system according to claim 13, wherein, in a case in which the radiographic image includes a plurality of the mammary gland regions, the second display processor displays the second position identification information items for the mammary gland regions in different forms.

15. The radiography system according to claim 1, wherein, in a case in which the first display processor changes a size of the radiographic image displayed on the display device, the second display processor performs control to change the display of the second position identification information, following the change in the size of the radiographic image.

16. The radiography system according to claim 1, wherein the second display processor performs control to audibly display the second position identification information.

17. The radiography system according to claim 1, wherein the compression member includes:
  a first compression member that compresses the breast; and
  a second compression member which is attachable to and detachable from the first compression member and to which the first position identification information is given.

18. A radiography system comprising:
  a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures a radiographic image of the breast in the compressed state using the radiation detector;
  a first display processor that performs control to display the radiographic image captured by the mammography apparatus on a display device; and
  a second display processor that performs control to display second position identification information which indicates a position on the radiographic image corresponding to the in-plane position of the compression member and corresponds to the first position identification information on the radiographic image displayed on the display device,
  wherein the second display processor performs control to display the second position identification information during continuous imaging, and the continuous imaging captures an ultrasound image of the breast while maintaining the compressed state after capturing the radiographic image and scanning the first surface of the compression member by using an ultrasonography apparatus, and
  wherein, in a case in which the continuous imaging is performed and the radiographic image includes a plurality of mammary gland regions, the second display processor displays the second position identification information in different forms in a mammary gland region for which the capture of the ultrasound image has ended and a mammary gland region for which the capture of the ultrasound image has not ended.

19. A control method comprising:
  performing control to display, on a display device, a radiographic image captured by a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures the radiographic image of the breast in the compressed state using the radiation detector; and
  performing control to display second position identification information which indicates a position on the radiographic image corresponding to the in-plane position of the compression member and corresponds to the first position identification information on the radiographic image displayed on the display device,
  wherein the control to display the second position identification information is performed during continuous imaging, and the continuous imaging captures an ultrasound image of the breast while maintaining the compressed state after capturing the radiographic image and scanning the first surface of the compression member by using an ultrasonography apparatus, and
  wherein, in a case in which the continuous imaging is performed and the radiographic image includes a plurality of mammary gland regions, the second position identification information is displayed in different forms in a mammary gland region for which the capture of the ultrasound image has ended and a mammary gland region for which the capture of the ultrasound image has not ended.

20. A control method comprising:
  performing control to display, on a display device, a radiographic image captured by a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device, wherein the control to display the second position identification information is performed during continuous imaging, and the continuous imaging captures an ultrasound image of the breast while maintaining the compressed state after capturing the radiographic image and scanning the first surface of the compression member by using an ultrasonography apparatus, and wherein, in a case in which the continuous imaging is performed and the radiographic image includes a plurality of mammary gland regions, the second position identification information is displayed in different forms in a mammary gland region for which the capture of the ultrasound image has ended and a mammary gland region for which the capture of the ultrasound image has not ended.

21. A non-transitory computer readable medium storing a control program that causes a computer to execute:

performing control to display, on a display device, a radiographic image captured by a mammography apparatus that includes a compression member which compresses a breast placed between a radiation source and a radiation detector and has a first surface irradiated with radiation from the radiation source and a second surface opposite to the first surface and coming into contact with the breast and in which first position identification information for identifying an in-plane position of the first surface or the second surface is given to any one of the first surface or the second surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device, wherein the control to display the second position identification information is performed during continuous imaging, and the continuous imaging captures an ultrasound image of the breast while maintaining the compressed state after capturing the radiographic image and scanning the first surface of the compression member by using an ultrasonography apparatus, and wherein, in a case in which the continuous imaging is performed and the radiographic image includes a plurality of mammary gland regions, the second position identification information is displayed in different forms in a mammary gland region for which the capture of the ultrasound image has ended and a mammary gland region for which the capture of the ultrasound image has not ended.

22. A non-transitory computer readable medium storing a control program that causes a computer to execute:

performing control to display, on a display device, a radiographic image captured by a mammography apparatus that includes a compression member which compresses a breast placed between a radiation source and a radiation detector and has a first surface irradiated with radiation from the radiation source, a second surface opposite to the first surface and coming into contact with the breast, and a third surface parallel to the first surface between the first surface and the second surface and in which first position identification information for identifying an in-plane position of the third surface is given to the third surface and that captures the radiographic image of the breast in the compressed state using the radiation detector; and performing control to display second position identification information which indicates a position on the radiographic image corresponding to the in-plane position of the compression member and corresponds to the first position identification information on the radiographic image displayed on the display device, wherein the control to display the second position identification information is performed during continuous imaging, and the continuous imaging captures an ultrasound image of the breast while maintaining the compressed state after capturing the radiographic image and scanning the first surface of the compression member by using an ultrasonography apparatus, and wherein, in a case in which the continuous imaging is performed and the radiographic image includes a plurality of mammary gland regions, the second position identification information is displayed in different forms in a mammary gland region for which the capture of the ultrasound image has ended and a mammary gland region for which the capture of the ultrasound image has not ended.

* * * * *